(12) United States Patent
Fuller et al.

(10) Patent No.: US 6,881,723 B1
(45) Date of Patent: Apr. 19, 2005

(54) NUCLEIC ACID CONSTRUCTS

(75) Inventors: Deborah L. Fuller, Middleton, WI (US); James T. Fuller, Middleton, WI (US)

(73) Assignee: Powderject Vaccines, Inc., Madison, WI (US)

( * ) Notice: Subject to any disclaimer, the term of this patent is extended or adjusted under 35 U.S.C. 154(b) by 0 days.

(21) Appl. No.: 09/434,830

(22) Filed: Nov. 5, 1999

Related U.S. Application Data

(60) Provisional application No. 60/115,405, filed on Jan. 8, 1999, and provisional application No. 60/107,169, filed on Nov. 5, 1998.

(51) Int. Cl.$^7$ ........................ A61K 48/00; C07H 21/04; C12N 15/74
(52) U.S. Cl. ..................... 514/44; 536/23.1; 435/320.1; 424/93.21
(58) Field of Search .......................... 514/44; 536/23.1; 435/320.1; 424/93.21

(56) References Cited

U.S. PATENT DOCUMENTS

| | | | |
|---|---|---|---|
| 4,599,230 A | 7/1986 | Milich et al. | |
| 4,599,231 A | 7/1986 | Milich et al. | |
| 4,629,782 A | 12/1986 | Chan et al. | |
| 4,945,050 A | 7/1990 | Sanford et al. | |
| 4,980,286 A | 12/1990 | Morgan et al. | |
| 4,981,782 A | 1/1991 | Judd et al. | |
| 5,036,006 A | 7/1991 | Sanford et al. | |
| 5,091,188 A | 2/1992 | Haynes | |
| 5,100,792 A | 3/1992 | Sanford et al. | |
| 5,120,657 A | 6/1992 | McCabe et al. | |
| 5,149,655 A | 9/1992 | McCabe | |
| 5,179,022 A | 1/1993 | Sanford et al. | |
| 5,204,253 A | 4/1993 | Sanford | |
| 5,371,015 A | 12/1994 | Sanford et al. | |
| 5,478,744 A | 12/1995 | Sanford et al. | |
| 5,584,807 A | 12/1996 | McCabe | |
| 5,589,466 A | 12/1996 | Felgner et al. | |
| 5,630,796 A | 5/1997 | Bellhouse et al. | |
| 5,658,892 A | 8/1997 | Flotte et al. | |
| 5,738,852 A | 4/1998 | Robinson et al. | |
| 5,865,796 A | 2/1999 | McCabe | |
| 5,899,880 A | 5/1999 | Bellhouse et al. | |
| 6,004,286 A | 12/1999 | Bellhouse et al. | |
| 6,010,478 A | 1/2000 | Bellhouse et al. | |
| 6,013,050 A | 1/2000 | Bellhouse et al. | |
| 6,194,389 B1 | 2/2001 | Johnston et al. | |
| 2002/0018766 A1 * | 2/2002 | Roberts et al. | 424/93.21 |

FOREIGN PATENT DOCUMENTS

| | | |
|---|---|---|
| CA | 1319628 | 8/1988 |
| EP | 0155146 | 9/1985 |
| EP | 0390435 A | 10/1990 |
| WO | WO 89/05349 | 6/1989 |
| WO | WO 90/01949 | 3/1990 |
| WO | WO 91/00359 | 1/1991 |
| WO | WO 91/07487 | 5/1991 |
| WO | WO 93/19183 | 9/1993 |
| WO | WO 94/09819 | 5/1994 |
| WO | WO 94/21797 | 9/1994 |
| WO | WO 94/24263 | 10/1994 |
| WO | WO 95/19799 | 7/1995 |
| WO | WO 95/20660 | 8/1995 |
| WO | WO 96/04947 | 2/1996 |
| WO | WO 96/12513 | 5/1996 |
| WO | WO 96/14855 | 5/1996 |
| WO | WO 96/20022 | 7/1996 |
| WO | WO 97/32987 | 9/1997 |
| WO | WO 97/40163 | 10/1997 |
| WO | WO 97/48485 | 12/1997 |
| WO | WO 98/10750 | 3/1998 |
| WO | WO 98/46263 | 10/1998 |

OTHER PUBLICATIONS

Londono et al, Vaccine 1996;14:545–52.*
Tindle et al, Virol 1994;200:547–57.*
Fuller et al, Vaccinces 96, Eds: Brown, Fred. Cold Spring Harbor Lab Press, Sep. 1995;87–91.*
Maryanski et al, Hum Immunol 1997;54:117–28.*
RA Strugnell et al., Immunology and Cell Biology, "DNA vaccines for bacterial infections," 1997, 75:364–369.*
Schodel F.et al. hybrid heaptitis B virus core antigen as a vaccine carrier moiety:I Presentation of foreign epitope. 1996, Jouranl of Bioteology, vol. 44 pp. 91–96.*
Milich D. et al. The hepatitis nucleocapsid as a vaccien carreir moiety. 1995, Ann. N.Y.Acad. Sci. vol. 754, pp. 187–201.*
Loktev V. et al. Design of immunogen as component of a new generatin of molecular vaccines. 1996, Jouranl of Bioteology, vol. 44 pp. 129–137.*
Leitner W. et al. DNA and RNA based vaccines: principles, progress and prospects. 2000, Vaccine, vol. 18, pp. 765–777.*
Bachmann m. et al, In vivo versus In vitor assays for assessment of T and B cell function. 1994, Current opinion in immunology, vol. 6, pp. 320–326.*
Orkin S. et al. Report and recommendatios of the panel to assess the NIH investment in research on gene therpay. 1995.*
Retorviruses, Ed. Coffin Cold Spring Harbor Press, 1997.*
Yasutomi et al. , A vaccine–elicited , single viral epitope–specific cytotoxic T lyphocyte response not protect against intravenous cell–free simsian immunodeficiency virus challenge. 1995, journal of virology, vol. 69,pp. 2279–2284.*

(Continued)

Primary Examiner—Q. Janice Li
(74) Attorney, Agent, or Firm—Foley & Lardner, LLP

(57) ABSTRACT

Recombinant nucleic acid molecules are described. The molecules have a first sequence encoding a Hepatitis B virus core antigen and a second sequence encoding at least one T cell epitope inserted within the first sequence. Vectors and compositions containing these molecules are also described. Methods of eliciting an immune response using these molecules are also described.

30 Claims, 3 Drawing Sheets

OTHER PUBLICATIONS

Schodel F. et al. The position of heterologous epitopes inserted in hepatitis B virus core particles. 1992, Journal of Virology, vol. 66, pp. 129–137.*

Schodel F. et al. inmmunity to malaria elicited by hybrid hepatitis B virus core particle carrying circumsporozoit protein epitopes. 1994, The journal of experimental medicine, vol. 180, pp. 1037–1046.*

Ciernik F. et al. Induction of cytotoxic T lymphocytes and antitumor immunity with DNA vaccines expressing single T cell epitopes. 1996, Journal of immunology, vol. 156, pp. 2369–2375.*

A. Aggarwal et al., "Oral *Salmonella:* Malaria Circumsporozoite Recombinants Induce Specific CD8+ Cytotoxic T Cells," The Journal of Experimental Medicine, vol. 172, pp. 1083–1090 (1990).

M. Del Val et al., "Protection Against Lethal Cytomegalovirus Infection by a Recombinant Vaccine Containing a Single Nonameric T–Cell Epitope," Journal of Virology, vol. 65, pp. 3641–3646 (1991).

D. Doolan et al., "Circumventing Genetic Restriction of Protection Against Malaria with Multigene DNA Immunization . . . ," The Journal of Experimental Medicine, vol. 183, pp. 1739–1746 (1996).

A. Malik, "Induction of Cytotoxic T Lymphocytes Against the *Plasmodium falciparum* Circumsporozoite Protein . . . ," Infection and Immunity, vol. 61, pp. 5062–5066 (1993).

W. Weiss et al., "Cytotoxic T Cells Recognize a Peptide from the Circumsporozoite Protein on Malaria–Infected Hepatocytes," The Journal of Experimental Medicine, vol. 171, pp. 763–773 (1990).

Haynes et al. (1991) *Mol. Immunology* 28:231–234.

Rhim et al. (1991) *J. Virology* 65:4555–4564.

Rousseaux–Prevost et al. (1991) *Molecular Immunology* 28:943–949.

Ferrari et al. (1991) *J. Clin. Invest.* 88:214–222.

Haynes et al. (1994) *Aids Res. and Human Retroviruses* 10(suppl..2):S43–S45.

Sedegah et al. (1994) *Proc. Natl. Acad. Sci. USA* 91:9866–9870.

Fuller et al. (1995) *Annals NY Acad Sci* 772:282–284.

Fynan et al. (1995) *Int. J. Immunopharmac.* 17:79–83.

Schodel et al. (1996) *Intervirology* 39:104–110.

Kuhrober et al.(1997) *Int. Immunol.* 9:1203–1212.

Schodel et al. (1992) *J. Virology* 66:106–114.

Remington's Pharmaceutical Sciences (1980) Mark Publishing Company, Pennsylvania, pp1483–1484 and 1535.

Townsend et al. (1984) *Cell* 39:13.

Townsend et al. (1985) *Prog. Allergy* 36:10.

Sanford et al. (1987) "Delivery of substances into cells and tissues using a particle bombardment process," *Particulate Science and Technology* 5:27–37.

Klein et al (1987) "High velocity microprojectiles for delivering nucleic acids into living cells," *Nature* 327:7–73.

Tang et al. (1988) *J. Virology* 62:4745–4751.

Zelenin et al. (1989) "Genetic transformation of mouse cultured cells with the help of high–velocity mechanical DNA injection," *FEBS Letters* 244:65–67.

Milich (1989) *Advances in Immunology* 45:195.

Schodel et al. (1989) *Infection and Immunity* 57:1347–1350.

Stahl et al. (1989) *Proc. Natl. Acad. Sci. USA* 86:6283–6287.

S.A. Johnston (1990) "Biolistic transformation: microbes to mice," *Nature* 346:776–777.

Poznansky et al. (1991) *J. Virology* 65:532–536.

* cited by examiner

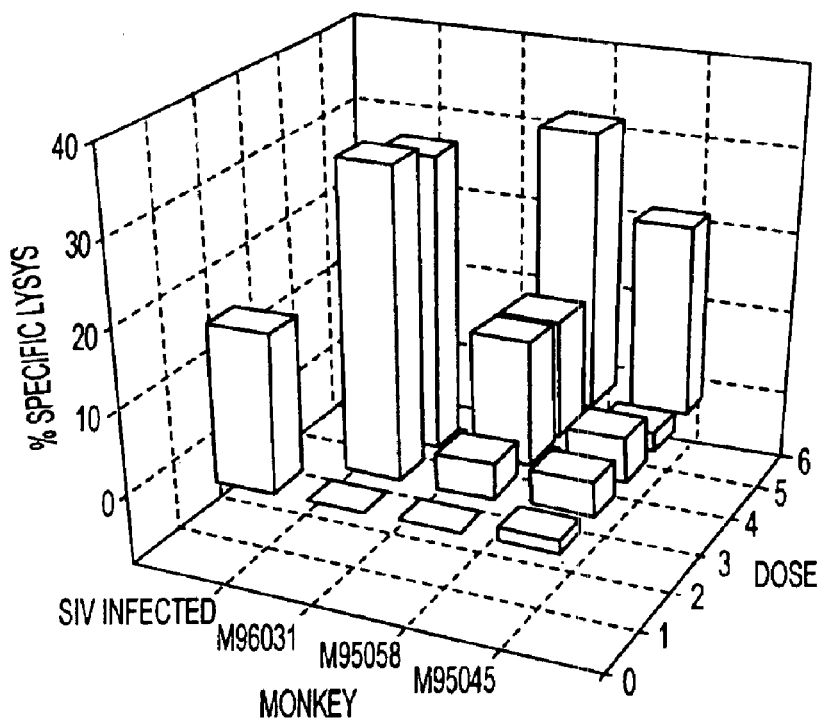

Induction of epitope-specific CD8+ T lymphocytes in an SIV infected monkey and three DNA-vaccinated monkeys. CD8+ T cell responses were measured after each of 5 DNA inoculations for monkeys 95058 and 95045 and each of 3 DNA inoculations for monkey 96031. PBMC were simulated for 2 weeks *in vitro* and then stained with tetameric complexes (Panel A) or tested in standard $^{51}$Cr-release assays (Panel B).

FIG. 2B

NUCLEIC ACID CONSTRUCTS

CROSS-REFERENCE TO RELATED APPLICATION

The application is related to U.S. provisional patent application Ser. No. 60/107,169, filed 5 Nov. 1998, from which application priority is claimed pursuant to U.S.C. § 119(e)(1) and which application is incorporated herein by reference in its entirety. The application is also related to U.S. provisional patent application Ser. No. 60/115,405, filed 8 Jan. 1999, from which application priority is claimed pursuant to 35 U.S.C. § 119(e)(1) and which application is incorporated herein by reference in its entirety.

TECHNICAL FIELD

The invention relates to the general fields of molecular biology and immunology, and generally relates to reagents useful in nucleic acid immunization techniques. More specifically, the invention relates to hybrid antigen/carrier nucleic acid constructs, expression vectors containing such constructs, and to nucleic acid immunization strategies employing such reagents.

BACKGROUND

Techniques for the injection of DNA and mRNA into mammalian tissue for the purposes of immunization against an expression product have been described in the art. See, e.g., European Patent Specification EP 0 500 799 and U.S. Pat. No. 5,589,466. The techniques, termed "nucleic acid immunization" herein, have been shown to elicit both humoral and cell-mediated immune responses. For example, sera from mice immunized with a DNA construct encoding the envelope glycoprotein, gp 160, were shown to react with recombinant gp 160 in immunoassays, and lymphocytes from the injected mice were shown to proliferate in response to recombinant gp120. Wang et al. (1993) Proc. Natl. Acad. Sci. USA 90:4156–4160. Similarly, mice immunized with a human growth hormone (hGH) gene demonstrated an antibody-based immune response. Tang et al. (1992) Nature 356:152–154. Intramuscular injection of DNA encoding influenza nucleoprotein driven by a mammalian promoter has been shown to elicit a CD8+ CTL response that can protect mice against subsequent lethal challenge with virus. Ulmer et al. (1993) Science 259:1745–1749. Immunohistochemical studies of the injection site revealed that the DNA was taken up by myeloblasts, and cytoplasmic production of viral protein could be demonstrated for at least 6 months.

SUMMARY OF THE INVENTION

It is a primary object of the invention to provide a recombinant nucleic acid molecule which includes a sequence encoding a hepatitis B virus nucelocapsid antigen (HBcAg) and a sequence encoding a T cell epitope of interest. It is preferred that the T cell epitope be a cytolytic T lymphocyte (CTL) epitope. The sequence encoding the epitope is inserted into the immunodominant core epitope (ICE) which is present in an externally accessible loop region of the HBcAg molecule, and the recombinant nucleic acid molecule is used as a reagent in various nucleic acid immunization strategies. The inserted sequence may also include one or more B cell epitopes of interest.

The HBcAg expression product self-assembles into a particle which is highly immunogenic in humans as well as in experimental animal model systems (Milich, D. R. (1988) Immunol. Today 9:380). For this reason, HBcAg particles have been used as a carrier moiety for chemically coupled or recombinant, translationally fused peptide epitopes (Clarke et al. (1987) Nature 330:381). In this regard, hybrid HBcAg molecules have been constructed which contain N-terminal or internal peptide epitope insertions, both of which approaches do not interfere with the ability of the core antigen to form particles. Isaguliants et al. (1996) Immunology Letters 52:37–44; Schödel et al. (1994) J. Exper. Med. 180:1037–1046. The resulting hybrid peptide particles have been used as subunit vaccine reagents with varying degrees of success, particularly to elicit an antibody response against an antigen of interest.

The present invention represents a significant departure from these previous efforts. That is, it has been found that, surprisingly, nucleic acid reagents which encode hybrid HBcAg molecules provide for an extremely high frequency cellular immune response against one or more CTL epitopes of interest contained within the hybrid molecules, particularly when the reagents are used in a DNA prime, recombinant viral vector boost immunization scheme. It has also been surprisingly found that this high frequency cellular response is driven by the hybrid HBcAg nucleic acid construct per se, and is thus not reproducible with other nucleic acid reagents.

Thus, in one aspect of the invention, a recombinant nucleic acid molecule is provided. The molecule has a first nucleic acid sequence which encodes a HBcAg carrier molecule that includes a primary immunodominant core epitope (ICE) loop region, and a second nucleic acid sequence which encodes an antigen of interest, wherein the antigen preferably contains at least one cytolytic T lymphocyte (CTL) epitope. The second nucleic acid sequence is heterologous to the first nucleic acid sequence, and is inserted into the sequence encoding the ICE loop region (in the first nucleic acid sequence). Placement of the second sequence directly into the ICE loop coding region is thought to disrupt the immunodominant core epitope, possibly decreasing the ability of a subject to mount an immune response against the HBcAg carrier component of the resultant hybrid molecule expression product. The subject recombinant nucleic acid molecule is a particularly superior reagent for use in nucleic acid immunizations, and can be used to elicit a high frequency CTL response against the antigen of interest in an immunized subject.

The fact that this molecule is so effective at eliciting a high frequency CTL response against an antigen placed within the ICE loop region (B cell immunodominant epitope region) is inherently counter-intuitive. This is because it is well accepted in the art that, for humoral responses, effective B cell epitopes are generally found in an externally accessible location (e.g., the ICE loop region of HBcAg) of the antigen molecule which allows for proper exposure to responding B cells. On the other hand, for cellular responses, peptide antigens must be processed into small fragments (epitopes) within a host subject's cells. These processed fragments can then enter the classical major histocompatibility complex (MHC) pathways for association with Class I and Class II MHC molecules on the cell surface, allowing for proper presentation to $CD8^+$ and $CD4^+$ T lymphocytes, respectively. For this reason, then, it is generally accepted that dominant T cell epitopes can be found anywhere in the antigen molecule (not necessarily in externally accessible locations), and often times occur at entirely different locations than dominant B cell epitopes in that same molecule.

In a related aspect of the invention, a recombinant nucleic acid molecule is provided which includes a first nucleic acid sequence that encodes an HBcAg carrier molecule from which the ICE region has been removed. The recombinant nucleic acid molecule also includes a second nucleic acid sequence that encodes an antigen of interest which contains at least one T cell epitope, preferably a CTL epitope. The second nucleic acid sequence is heterologous to the first nucleic acid sequence, and the first and second nucleic acid sequences are linked together to form a hybrid sequence. In particular embodiments, the sequence encoding the ICE loop region is replaced with the second nucleic acid sequence so that the antigen of interest will be arranged within the loop portion of the expressed hybrid HbcAg carrier molecule. In other embodiments, the second nucleic acid sequence is positioned within the nucleic acid molecule such that it winds up in an N-terminal, C-terminal or internal portion of the resultant hybrid core carrier molecule. In these various embodiments, it is preferred that the second sequence is arranged within the molecule in a position where it will not interfere with particle formation of the expression product. Here again, the preference that the recombinant nucleic acid molecule encode a hybrid HBcAg carrier that will self-assemble into a particulate antigen is slightly counter-intuitive since the high frequency CTL response against the antigen of interest is driven by intercellular processing of peptide fragments and MHC Class I presentation. Although not wishing to be bound by any particular theory, a possible reason for favoring those hybrid molecules which retain the ability to form particles is that the particles are more efficiently secreted by a host's cells, allowing for a broader and more sustained exposure of the antigen to a host's immune processing cells. Another possible reason is that reasonably stable hybrid particles will have access to the exogenous Class I pathway.

In a still further related aspect of the invention, the recombinant nucleic acid molecules of the present invention include a third nucleic acid sequence which encodes a peptide leader sequence. The third sequence is arranged in the molecule in a 5' upstream position relative to the second and third nucleic acid sequences, and is linked to these other sequences to form a hybrid sequence. The encoded leader sequence provides for efficient secretion of the encoded hybrid HBcAg carrier molecules from cells transfected with the subject recombinant nucleic acid molecules. In yet another related aspect of the invention, the recombinant nucleic acid molecule includes a first sequence encoding a HBcAg which has had the C-terminal arginine-rich region removed. All of the recombinant nucleic acid molecules of the present invention are typically provided in the form of an expression cassette which contains the necessary sequences to control the expression of the nucleic acid molecules. These expression cassettes, in turn, are typically provided within vectors (e.g., plasmids or recombinant viral vectors) which are suitable for use as reagents for nucleic acid immunization.

It is also a primary object of the invention to provide a method for eliciting a cellular immune response against an antigen of interest in an immunized subject. The method entails a primary immunization step comprising one or more steps of transfecting cells of the subject with a recombinant nucleic acid molecule encoding a hybrid molecule having a HBcAg carrier component and a target antigen component comprising at least one T cell epitope of interest, preferably a cytolytic T lymphocyte (CTL) epitope. Expression cassettes and/or vectors including any one of the recombinant nucleic acid molecules of the present invention can be used to transfect the cells, and transfection is carried out under conditions that permit expression of the hybrid molecule within the subject. The method further entails a secondary, or booster immunization step comprising one or more steps of administering a secondary composition to the subject, wherein the secondary composition comprises the at least one epitope from the target antigen. The combination of the primary and secondary immunization steps is sufficient to elicit a cellular response against the target antigen.

The transfection procedure carried out during the primary immunization step can be conducted either in vivo, or ex viva (e.g., to obtain transfected cells which are subsequently introduced into the subject prior to carrying out the secondary immunization step). When in vivo transfection is used, the nucleic acid molecule can be administered to the subject by way of intramuscular or intradermal injection of plasmid DNA or, preferably, administered to the subject using a particle-mediated delivery technique. The secondary composition can include the antigen of interest in the form of any suitable vaccine composition, for example, in the form of a peptide subunit vaccine composition, in the form of hybrid HBcAg particles, in the form of a further nucleic acid vaccine composition (e.g., containing the antigen alone, or containing the entire gene sequence that includes the antigen), or in the form of a recombinant viral vector which contains a coding sequence for the antigen of interest. In particular embodiments, the secondary composition includes a recombinant vaccinia viral vector, for example a modified vaccinia Ankara (MVA) viral vector, which contains a sequence encoding the at least one CTL epitope from the target antigen.

The recombinant nucleic acid encoding a hybrid molecule having a HBcAg carrier component and a target antigen component comprising at least one T cel epitope of interest (preferably a CTL epitope) can also be used as a boosting agent, such as in a vaccination strategy where an individual is primed with any suitable vaccine composition that contains an antigen of interest, for example, in the form of a peptide subunit vaccine composition, a whole or split organism vaccine composition (e.g., whole virus, attenuated or inactivated virus, etc.), a nucleic acid vaccine composition, a recombinant viral vaccine composition, or the like.

It is an advantage of the invention that the recombinant nucleic acid molecules can be used as reagents in nucleic acid immunization strategies to attain a high-frequency CTL response against one or more antigens of interest. It is a further advantage of the invention that these high frequency CTL responses are useful in both prophylactic and therapeutic vaccine contexts.

These and other objects, aspects, embodiments and advantages of the present invention will readily occur to those of ordinary skill in the art in view of the disclosure herein.

BRIEF DESCRIPTION OF THE FIGURES

FIGS. 2A and 2b depict the results of assays carried out in Example 2.

DETAILED DESCRIPTION OF THE PREFERRED EMBODIMENTS

Figure 1:
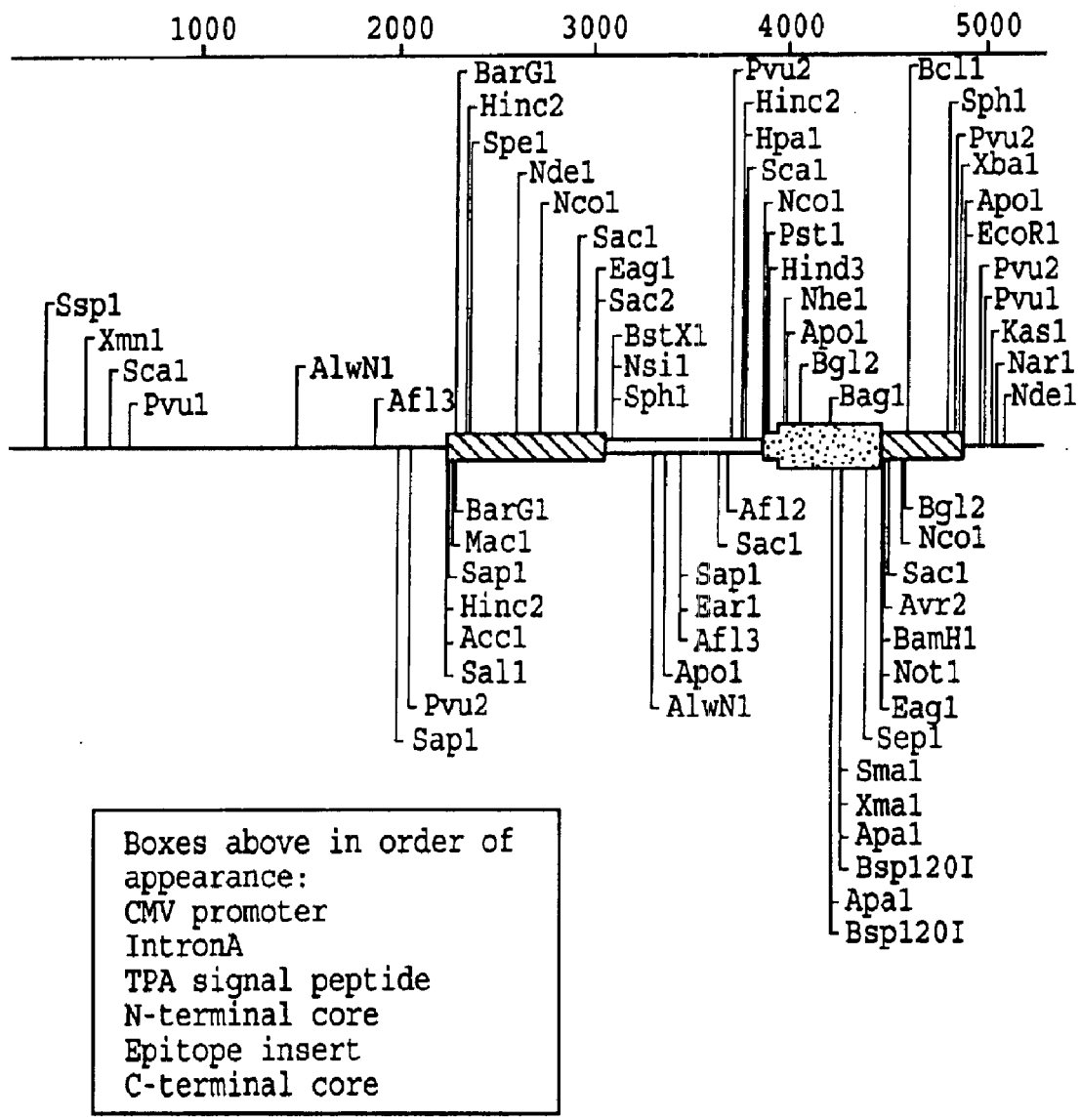
FIG. 1 depicts a plasmid map identifying the major components of a plasmid vector constructed according to the present invention.
Figure 2A:
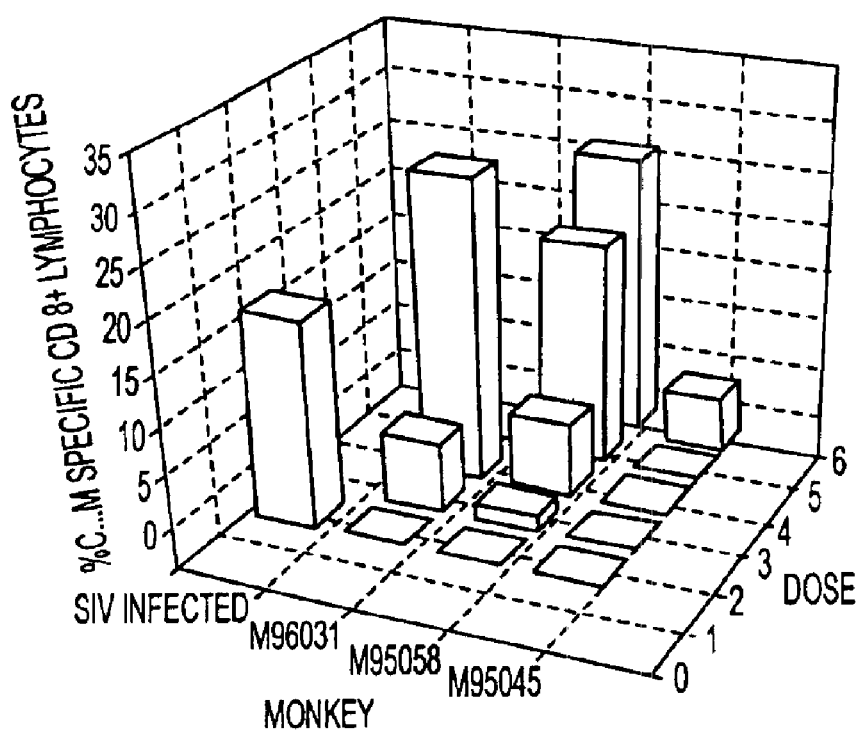

Before describing the present invention in detail, it is to be understood that this invention is not limited to particularly exemplified molecules or process parameters as such may, of course, vary. It is also to be understood that the terminology used herein is for the purpose of describing particular embodiments of the invention only, and is not intended to be limiting. In addition, the practice of the present invention will employ, unless otherwise indicated, conventional methods of virology, microbiology, molecular biology, recombinant DNA techniques and immunology all of which are within the ordinary skill of the art. Such techniques are explained fully in the literature. See, e.g., Sambrook, et al., *Molecular Cloning: A Laboratory Manual* (2nd Edition, 1989); *DNA Cloning: A Practical Approach*, vol. I & II (D. Glover, ed.); *Oligonucleotide Synthesis* (N. Gait, ed., 1984); *A Practical Guide to Molecular Cloning* (1984); and *Fundamental Virology*, 2nd Edition, vol. I & II (B. N. Fields and D. M. Knipe, eds.).

All publications, patents and patent applications cited herein, whether supra or infra, are hereby incorporated by reference in their entirety.

It must be noted that, as used in this specification and the appended claims, the singular forms "a," "an" and "the" include plural referents unless the content clearly dictates otherwise. Thus, reference to "a CTL epitope" includes two or more such epitopes, reference to "an antigen" includes two or more such antigens, and the like.

A. Definitions

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed, and are intended to be defined as indicated below.

The term "nucleic acid immunization" is used herein to refer to the introduction of a nucleic acid molecule encoding one or more selected antigens into a host cell for the in vivo expression of the antigen or antigens. The nucleic acid molecule can be introduced directly into the recipient subject, such as by standard intramuscular or intradermal injection; transdermal particle delivery; inhalation; topically, or by oral, intranasal or mucosal modes of administration. The molecule alternatively can be introduced ex vivo into cells which have been removed from a subject. In this latter case, cells containing the nucleic acid molecule of interest are introduced into the subject such that an immune response can be mounted against the antigen encoded by the nucleic acid molecule.

An "antigen" refers to any agent, generally a macromolecule, which can elicit an immunological response in an individual. The term may be used to refer to an individual macromolecule or to a homogeneous or heterogeneous population of antigenic macromolecules. As used herein, "antigen" is generally used to refer to a protein molecule or portion thereof which contains one or more epitopes. For purposes of the present invention, antigens can be obtained or derived from any known virus, bacteria, parasite or fungal pathogen. The term also intends any of the various tumor-specific antigens and antigens associated with autoimmune diseases. Furthermore, for purposes of the present invention, an "antigen" includes a protein having modifications, such as deletions, additions and substitutions (generally conservative in nature) to the native sequence, so long as the protein maintains sufficient immunogenicity. These modifications may be deliberate, for example through site-directed mutagenesis, or may be accidental, such as through mutations of hosts which produce the antigens.

In various aspects of the invention, the antigen contains one or more T cell epitopes. A "T cell epitope" refers generally to those features of a peptide structure which are capable of inducing a T cell response. In this regard, it is accepted in the art that T cell epitopes comprise linear peptide determinants that assume extended conformations within the peptide-binding cleft of MHC molecules. Unanue et al. (1987) *Science* 236:551–557. As used herein, a T cell epitope is generally a peptide having at least about 3–5 amino acid residues, and preferably at least 5–10 or more amino acid residues. The term encompasses any MHC Class I- or MHC Class II-restricted peptide. The ability of a particular epitope to stimulate a cell-mediated immunological response may be determined by a number of well-known assays, such as by lymphoproliferation (lymphocyte activation) assays, CTL cytotoxic cell assays, or by assaying for T-lymphocytes specific for the epitope in a sensitized subject. See, e.g., Erickson et al. (1993)*J. Immunol.* 151:4189–4199; and Doe et al. (1994) *Eur. J. Immunol.* 24:2369–2376.

In other aspects of the invention, the antigen contains one or more B cell epitopes. A "B cell epitope" generally refers to the site on an antigen to which a specific antibody molecule binds. The identification of epitopes which are able to elicit an antibody response is readily accomplished using techniques well known in the art. See, e.g., Geysen et al. (1984) *Proc. Natl. Acad. Sci. USA* 81:3998–4002 (general method of rapidly synthesizing peptides to determine the location of immunogenic epitopes in a given antigen); U.S. Pat. No. 4,708,871 (procedures for identifying and chemically synthesizing epitopes of antigens); and Geysen et al. (1986) *Molecular Immunology* 23:709–715 (technique for identifying peptides with high affinity for a given antibody).

An "immune response" against an antigen of interest is the development in an individual of a humoral and/or a cellular immune response to that antigen. For purposes of the present invention, a "humoral immune response" refers to an immune response mediated by antibody molecules, while a "cellular immune response" is one mediated by T-lymphocytes and/or other white blood cells.

When an individual is immunized with a complex protein antigen having multiple determinants (epitopes), in many instances the majority of responding T lymphocytes will be specific for one or a few linear amino acid sequences (epitopes) from that antigen and/or a majority of the responding B lymphocytes will be specific for one or a few linear or conformational epitopes from that antigen. For the purposes of the present invention, then, such epitopes are referred to as "immunodominant epitopes." In an antigen having several immunodominant epitopes, a single epitope may be the most dominant in terms of commanding a specific T or B cell response. Thus, for the purposes of the present invention, the term "primary immunodominant epitope" is used to refer to the most dominant immunodominant epitope from an antigen having a plurality of such epitopes, and the remaining immunodominant epitopes are referred to as "secondary immunodominant epitope(s)." The hepatitis B virus nucleocapsid antigen (HBcAg) contains an N-terminal immunodominant CTL epitope occurring at about residues 18–27 of the wild-type amino acid sequence. The HBcAg also has a dominant B cell epitope occurring at an internal position in the HBcAg particle (occurring at about residues 74–81 of the wild type amino acid sequence). This dominant HBcAg B cell epitope is referred to herein as the "immunodominant core epitope" loop region, or "ICE" loop region since it is exposed as a surface-accessible loop structure (a "solvent accessible" loop) in the formed core antigen particle.

A "coding sequence," or a sequence which "encodes" a selected antigen, is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, a coding sequence can include, but is not limited to, cDNA from viral, procaryotic or eucaryotic mRNA, genomic DNA sequences from viral or procaryotic DNA, and even synthetic DNA sequences. A transcription termination sequence may be located 3' to the coding sequence.

A "nucleic acid" molecule can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Recombinant" is used herein to describe a nucleic acid molecule (polynucleotide) of genomic, cDNA, semisynthetic, or synthetic origin which, by virtue of its origin or manipulation is not associated with all or a portion of the polynucleotide with which it is associated in nature and/or is linked to a polynucleotide other than that to which it is linked in nature. Two nucleic acid sequences which are contained within a single recombinant nucleic acid molecule are "heterologous" relative to each other when they are not normally associated with each other in nature.

Two nucleic acid sequences are "substantially homologous" when at least about 70%, preferably at least about 80–90%, and most preferably at least about 95%, of the nucleotides match over a defined length of the molecule. As used herein, substantially homologous also refers to sequences showing identity to the specified nucleic acid. Nucleic acid sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, vols I & II, supra; *Nucleic Acid Hybridization*, supra. Such sequences can also be confirmed and further characterized by direct sequencing of PCR products.

The terms "individual" and "subject" are used interchangeably herein to refer to any member of the subphylum cordata, including, without limitation, humans and other primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs; birds, including domestic, wild and game birds such as chickens, turkeys and other gallinaceous birds, ducks, geese, and the like. The terms do not denote a particular age. Thus, both adult and newborn individuals are intended to be covered. The methods described herein are intended for use in any of the above vertebrate species, since the immune systems of all of these vertebrates operate similarly.

B. General Methods

In one embodiment, a recombinant nucleic acid molecule is provided. The recombinant molecule includes a sequence encoding a hepatitis B virus nucleocapsid antigen (HBcAg) and a sequence encoding a cytolytic T lymphocyte (CTL) epitope of interest. The sequence encoding the CTL epitope can be inserted into the immunodominant core epitope (ICE) loop region of the HBcAg molecule. Alternatively, the ICE region can be deleted from the molecule, and the sequence encoding the CTL epitope can inserted in place of the ICE region, or inserted into any other N-terminal, C-terminal or internal position of the HBcAg portion of the molecule. It is preferred that insertion of the sequence encoding the CTL epitope into the HBcAg portion of the hybrid molecule does not interfere with the ability of the expression product to self-assemble into a hybrid core carrier particle. When transfected into an appropriate host cell, the recombinant nucleic acid molecule encodes a hybrid HBcAg carrier moiety, wherein the HBcAg portion serves as a carrier, and the CTL epitope portion serves as the immunogen. The recombinant nucleic acid molecules of the present invention can be used as reagents in various nucleic acid immunization strategies.

The HBcAg portion of the recombinant nucleic acid molecule can be obtained from known sources. In this regard, the hepatitis B virus (HBV) is a small, enveloped virus with a double-stranded DNA genome. The sequence of the HBV genome (e.g., particularly of subtypes adw and ayw) is known and well characterized. Tiollais et al. (1985) *Nature* 317:489, Chisari et al. (1989) *Microb. Pathog.* 6:311. The HBcAg is a polypeptide comprised of 180 amino acid residues and has several immunodominant portions which have been highly studied (e.g., the ICE loop region). HBcAg can be readily expressed in *Escherichia coli* and other prokaryotes where it self-assembles into particles. For this reason, numerous peptide antigens have been fused to the HBcAg to provide hybrid core carrier particles that exhibit enhanced B cell immunogenicity. Schödel et al. (1994) *J. Exper. Med.* 180:1037; Clarke et al. (1987) *Nature* 330:381; Borisova et al. (1989) *FEBS Lett.* 259:121; Stahl et al. (1989) *Proc. natl. Acad. Sci. USA* 86:6283. The nucleic acid sequence encoding the HBcAg is also known, and plasmid constructs containing the HBcAg sequence have been described. Schödel et al., supra. In the expression product, the immunodominant loop region spans residues 72–85 of the 180 residue HBcAg molecule, with the ICE occurring at about residues 74–81.

In like manner, the nucleic acid sequence encoding the antigen of interest can also be obtained from known sources. In this regard, the antigen of interest will preferably be associated with a pathogen, such as a viral, bacterial or parasitic pathogen, or the antigen may be a tumor-specific antigen or an antigen useful in breaking self-tolerance in autoimmune disorders such as in diabetes, lupus, arthritis, MS and in allergy.

Tumor-specific antigens include, but are not limited to, any of the various MAGEs (melanoma associated antigen E), including MAGE 1, MAGE 2, MAGE 3 (HLA-A1 peptide), MAGE 4, etc.; any of the various tyrosinases (HLA-A2 peptide); mutant ras; mutant p53; and p97 melanoma antigen. Other tumor-specific antigens include the Ras peptide and p53 peptide associated with advanced cancers, the HPV 16/18 and E6/E7 antigens associated with cervical cancers, MUC1-KLH antigen associated with breast carcinoma, CEA (carcinoembryonic antigen) associated with colorectal cancer, gp100 or MART1 antigens associated with melanoma, and the PSA antigen associated with prostate cancer. The p53 gene sequence is known (see e.g., Harris et al. (1986) *Mol. Cell. Biol.* 6:4650–4656) and is deposited with GenBank under Accession No. M14694.

Suitable viral antigens include, but are not limited to, polynucleotide sequences encoding antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV). By way example and not limiting in the present invention, the genomic sequence of HCV is known, as well as methods for obtaining the sequence. See, e.g., International Publication Nos. WO 89/04669; WO 90/11089; and WO 90/14436. Similarly, the coding sequence for the δ-antigen from HDV is known (see, e.g., U.S. Pat. No. 5,378,814).

Sequences encoding a wide variety of protein antigens from the herpesvirus family can also be used in the practice of the present invention, including antigens derived from herpes simplex virus (HSV) types 1 and 2, such as HSV-1 and HSV-2 glycoproteins gB, gD and gH; antigens from varicella zoster virus (VZV), Epstein-Barr virus (EBV) and cytomegalovirus (CMV) including CMV gB and gH; and antigens from other human herpesviruses such as HHV6 and HHV7. (See, e.g. Chee et al. (1990) *Cytomegaloviruses* (J. K. McDougall, ed., Springer-Verlag, pp. 125–169; McGeoch et al. (1988)*J. Gen. Virol.* 69:1531–1574; U.S. Pat. No. 5,171,568; Baer et al. (1984) *Nature* 310:207–211; and Davison et al. (1986)*J. Gen. Virol.* 67:1759–1816.)

HIV antigens, such as the gp120 sequences for a multitude of HIV-1 and HIV-2 isolates, including members of the various genetic subtypes of HIV, are known and reported (see, e.g., Myers et al., Los Alamos Database, Los Alamos National Laboratory, Los Alamos, N. Mex. (1992); and Modrow et al. (1987) *J. Virol.* 61:570–578) and antigens derived from any of these isolates will find use in the present methods. Furthermore, the invention is equally applicable to other immunogenic moieties derived from any of the various HIV isolates, including any of the various envelope proteins such as gp 160 and gp41, gag antigens such as p24gag and p55gag, as well as proteins derived from the pol, env, tat, vif rev, nef vpr, vpu and LTR regions of HIV.

Influenza virus antigens, particularly, the envelope glycoproteins HA and NA of influenza A, are also well known and widely characterized. In this regard, numerous HA subtypes of influenza A have been identified (Kawaoka et al. (1990) *Virology* 179:759; Webster et al., "Antigenic variation among type A influenza viruses," p. 127–168. In: P. Palese and D. W. Kingsbury (ed.), *Genetics of influenza viruses*. Springer-Verlag, N.Y.).

Sequences encoding antigens derived or obtained from other viruses will also find use in the practice of the invention including, without limitation, sequences from members of the families Picomaviridae (e.g., polioviruses, FMDV, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM}235$, $HIV-1_{US4}$; HIV-2, among others. See, e.g., *Virology*, 3rd Edition (W. K. Joklik ed. 1988); *Fundamental Virology*, 2nd Edition (B. N. Fields and D. M. Knipe, eds. 1991), for a description of these and other viruses.

Sequences encoding suitable bacterial and parasitic antigens can be obtained or derived from known causative agents responsible for diseases such as Diptheria, Pertussis, Tetanus, Tuberculosis, Bacterial or Fungal Pneumonia, Cholera, Typhoid, Plague, Shigellosis or Salmonellosis, Legionaire's Disease, Lyme Disease, Leprosy, Malaria, Hookworm, Onchocerciasis, Schistosomiasis, Trypamasomialsis, Lesmaniasis, *Giardia*, Amoebiasis, Filariasis, *Borelia*, and Trichinosis. Still further antigen sequences can be obtained or derived from unconventional viruses or prions such as the causative agents of kuru, Creutzfeldt-Jakob disease (CJD), scrapie, transmissible mink encephalopathy, and chronic wasting diseases, or from proteinaceous infectious particles such as prions that are associated with mad cow disease.

The selected antigen sequence can be used as a discrete antigen, e.g., as a sequence encoding a short peptide, or a minigene (Yu et al.) or larger portions of a molecule or genome in question can be used, for example, a proviral DNA which includes nearly all of a particular viral genome. Multiple antigens can also be used, either from the same entity or from an entirely unrelated entity. However, each antigen of interest which is included within the recombinant nucleic acid molecules of the present invention will contain at least one T cell epitope, preferably a CTL epitope. The presence of a T cell epitope in a particular antigen sequence can be readily determined by those skilled in the relevant art. For example, common computer software packages and peptide simulation techniques can be used to scan a given sequence for the presence of ideal, allele-specific MHC binding motifs. Rothbard et al. (1991) *Ann. Rev. Immunol.* 9:527; Rotzschke et al. (1991) *Immunol. Today* 12:447; Bertoletti et al. (1993) *J. Virol.* 67:2376; Flak et al. (1991) *Nature* 351:290.

In some molecules, a third, ancillary sequence can be included which provides for secretion of an attached hybrid HBcAg-antigen molecule from a mammalian cell. Such secretion leader sequences are known to those skilled in the art, and include, for example, the tissue plasminogen activator (tpa) leader signal sequence.

The sequences for the HBcAg carrier, the ancillary leader, and the antigen(s) of interest can be obtained and/or prepared using known methods. For example, substantially pure antigen preparations can be obtained using standard molecular biological tools. That is, polynucleotide sequences coding for the above-described moieties can be obtained using recombinant methods, such as by screening cDNA and genomic libraries from cells expressing an antigen, or by deriving the coding sequence for the HBcAg from a vector known to include the same. Furthermore, the desired sequences can be isolated directly from cells and tissues containing the same, using standard techniques, such as phenol extraction and PCR of cDNA or genomic DNA. See, e.g., Sambrook et al., supra, for a description of techniques used to obtain and isolate DNA. Polynucleotide sequences can also be produced synthetically, rather than cloned.

Yet another convenient method for isolating specific nucleic acid molecules is by the polymerase chain reaction (PCR). Mullis et al., (1987) *Methods Enzymol.* 155:335–350. This technique uses DNA polymerase, usually a thermostable DNA polymerase, to replicate a desired region of DNA. The region of DNA to be replicated is identified by oligonucleotides of specified sequence complementary to opposite ends and opposite strands of the desired DNA to prime the replication reaction. The product of the first round of replication is itself a template for subsequent replication, thus repeated successive cycles of replication result in geometric amplification of the DNA fragment delimited by the primer pair used.

Once the sequences for the HBcAg carrier and the antigen(s) of interest have been obtained, they are linked together to provide a nucleic acid molecule using standard cloning or molecular biology techniques. More particularly, after the sequence information for the HBcAg carrier is obtained, the sequence encoding the antigen of interest is combined with the carrier sequence to form the hybrid molecule. As described herein above, the antigen sequence can simply be placed within the ICE loop region, thereby disrupting that region, or the ICE loop region can be deleted from the carrier portion of the molecule and either replaced with the antigen sequence, or the antigen sequence can be arranged at a different location within the HBcAg sequence. The antigen sequence which encodes at least one T cell epitope (e.g., a CTL epitope) will generally encode a minimum of about five amino acids, more typically a minimum of about eight amino acids, and even more typically, a minimum of about 9–10 amino acids. If more than one epitope is present, the antigen sequence will be at least as big as the combined sequences of the epitopes. However, since T cell epitopes can overlap, the minimum amino acid sequence for the antigen sequence may be less than the sum of the individual epitopes.

Although any number of routine molecular biology techniques can be used to construct such recombinant nucleic acid molecules, one convenient method entails using one or more unique restriction sites in the HBcAg sequence (or inserting one or more unique restriction sites into the HBcAg sequence) and standard cloning techniques to direct the antigen sequence into a particular target location within the carrier sequence. In this regard, the design of unique restriction sites is readily accomplished by either analyzing the HBcAg sequence for existing restriction sites, or by subjecting the HBcAg sequence to a battery of different restriction endonucleases and determining which enzymes cleave the sequence and the site of each cleavage. Sequences already present in the HBcAg molecule that flank a particular targeted insertion site can be mutated to produce a unique restriction site. Otherwise suitable restriction sites can be readily inserted (e.g., engineered) into the HIBcAg sequence to provide for one or more target insertion sites. The antigen sequence(s) will thus, of course, be manipulated to have flanking restriction sites which correspond with the target site in the HBcAg sequence. In this manner, antigen sequences can be readily shuttled into and out of the HBcAg sequence.

Alternatively, the hybrid carrier/antigen sequence can be produced synthetically, rather than cloned. The nucleotide sequence can be designed with the appropriate codons for the particular amino acid sequence desired. In general, one will select preferred codons for the intended host in which the sequence will be expressed. The complete sequence can then be assembled from overlapping oligonucleotides prepared by standard methods and assembled into a complete coding sequence. See, e.g., Edge (1981) Nature 292:756; Nambair et al. (1984) Science (1984) 223:1299; Jay et al. (1984) J. Biol. Chem. 259:6311.

In whatever manner that the recombinant nucleic acid molecule is prepared, it is preferred that insertion of the antigen sequence(s) into the HBcAg carrier is such that it does not disrupt the ability of the hybrid core carrier expression product to self-assemble into particles. The ability of a hybrid HBcAg-antigen molecule expression product to form particles can be assessed using known techniques (see, e.g., Schödel et al., supra, electron micrographs of fixed particles, negative stain).

Once the antigen sequence has been inserted into the HBcAg sequence to obtain the recombinant nucleic acid molecule, this hybrid coding sequence can be inserted into a vector which includes control sequences operably linked to the inserted sequence, thus allowing for expression of the hybrid HBcAg-antigen molecule in vivo in a targeted subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and other suitably efficient promoter systems. Nonviral promoters, such as a promoter derived from the murine metallothionein gene, may also be used for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence. Introns, containing splice donor and acceptor sites, may also be designed into the expression cassette.

In addition, enhancer elements may be included within the expression cassettes in order to increase expression levels. Examples of suitable enhancers include the SV40 early gene enhancer (Dijkema et al. (1985) EMBO J. 4:761), the enhancer/promoter derived from the long terminal repeat (LTR) of the Rous Sarcoma Virus (Gorman et al. (1982) Proc. Natl. Acad. Sci. USA 79:6777), and elements derived from human or murine CMV (Boshart et al. (1985) Cell 41:521), for example, elements included in the CMV intron A sequence.

Once complete, these constructs are used for nucleic acid immunization using standard gene delivery protocols. Methods for gene delivery are known in the art. See, e.g., U.S. Pat. Nos. 5,399,346, 5,580,859, 5,589,466. Genes can be delivered either directly to a subject or, alternatively, delivered ex vivo to cells derived from the subject whereafter the cells are reimplanted in the subject.

A number of viral based systems have been developed for transfecting mammalian cells. For example, a selected recombinant nucleic acid molecule can be inserted into a vector and packaged as retroviral particles using techniques known in the art. The recombinant virus can then be isolated and delivered to cells of the subject either in vivo or ex vivo. A number of retroviral systems have been described (U.S. Pat. No. 5,219,740; Miller et al. (1989) BioTechniques 7:980–990; Miller, A. D. (1990) Human Gene Therapy 1:5–14; and Burns et al. (1993) Proc. Natl. Acad. Sci. USA 90:8033–8037.

A number of adenovirus vectors have also been described (Haj-Ahmad et al. (1986) J. Virol. 57:267–274; Bett et al. (1993) J. Virol. 67:5911–5921; Mittereder et al. (1994) Human Gene Therapy 5:717–729; and Rich et al. (1993) Human Gene Therapy 4:461–476). Additionally, various adeno-associated virus (AAV) vector systems have been developed. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al. (1988) Molec. Cell. Biol. 8:3988–3996; Vincent et al. (1990) Vaccines 90 (Cold Spring Harbor Laboratory Press); Carter, B. J. (1992) Current Opinion in Biotechnology 3:533–539; Muzyczka, N. (1992) Current Topics in Microbiol. and Immunol. 158:97–129; and Kotin, R. M. (1994) Human Gene Therapy 5:793–801. Additional viral vectors which will find use for delivering the recombinant nucleic acid molecules of the present invention include, but are not limited to, those derived from the pox family of viruses, including vaccinia virus and avian poxvirus.

If viral vectors are not wanted, liposomal preparations can alternatively be used to deliver the nucleic acid molecules of the invention. Useful liposomal preparations include cationic (positively charged), anionic (negatively charged) and neutral preparations, with cationic liposomes particularly preferred. Cationic liposomes have been shown to mediate intracellular delivery of plasmid DNA (Feigner et al. (1987) Proc. Natl. Acad. Sci. USA 84:7413–7416) and mRNA (Malone et al. (1989) *Proc. Natl. Acad. Sci. USA* 86:6077–6081).

As yet another alternative to viral vector systems, the nucleic acid molecules of the present invention may be encapsulated, adsorbed to, or associated with, particulate carriers. Suitable particulate carriers include those derived from polymethyl methacrylate polymers, as well as PLG microparticles derived from poly(lactides) and poly(lactide-co-glycolides). See, e.g., Jeffery et al. (1993) *Pharm. Res.* 10:362–368. Other particulate systems and polymers can also be used, for example, polymers such as polylysine, polyarginine, polyornithine, spermine, spermidine, as well as conjugates of these molecules.

Formulation of a composition comprising the above recombinant nucleic acid molecules can be carried out using standard pharmaceutical formulation chemistries and methodologies all of which are readily available to the reasonably skilled artisan. For example, compositions containing one or more nucleic acid molecules can be combined with one or more pharmaceutically acceptable excipients or vehicles. Auxiliary substances, such as wetting or emulsifying agents, pH buffering substances and the like, may be present in the excipient or vehicle. These excipients, vehicles and auxiliary substances are generally pharmaceutical agents that do not induce an immune response in the individual receiving the composition, and which may be administered without undue toxicity. Pharmaceutically acceptable excipients include, but are not limited to, liquids such as water, saline, polyethyleneglycol, hyaluronic acid, glycerol and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Certain facilitators of nucleic acid uptake and/or expression can also be included in the compositions, for example, facilitators such as bupivacaine, cardiotoxin and sucrose. A thorough discussion of pharmaceutically acceptable excipients, vehicles and auxiliary substances is available in REMINGTON'S PHARMACEUTICAL SCIENCES (Mack Pub. Co., N.J. 1991), incorporated herein by reference.

The formulated compositions will include an amount of the antigen of interest which is sufficient to mount an immunological response, as defined above. An appropriate effective amount can be readily determined by one of skill in the art. Such an amount will fall in a relatively broad range that can be determined through routine trials. The compositions may contain from about 0.1% to about 99.9% of the antigen and can be administered directly to the subject or, alternatively, delivered ex vivo, to cells derived from the subject, using methods known to those skilled in the art. For example, methods for the ex vivo delivery and reimplantation of transformed cells into a subject are known (e.g., dextran-mediated transfection, calcium phosphate precipitation, electroporation, and direct microinjection of into nuclei). Methods for in vivo delivery can entail injection using a conventional syringe. The constructs can be injected either subcutaneously, epidermally, intradermally, intramucosally such as nasally, rectally and vaginally, intraperitoneally, intravenously, orally or intramuscularly. Other modes of administration include oral and pulmonary administration, suppositories, and transdermal applications.

It is preferred, however, that the nucleic acid molecules be delivered using a particle acceleration device which fires nucleic acid-coated microparticles into target tissue, or transdermally delivers particulate nucleic acid compositions. In this regard, gene gun-based nucleic acid immunization has been shown to elicit both humoral and cytotoxic T lymphocyte immune responses following epidermal delivery of nanogram quantities of DNA. Pertmer et al. (1995) *Vaccine* 13:1427–1430. Particle-mediated delivery techniques have been compared to other types of nucleic acid inoculation, and found markedly superior. Fynan et al. (1995) *Int. J. Immunopharmacology* 17:79–83, Fynan et al. (1993) *Proc. Natl. Acad. Sci. USA* 90:11478–11482, and Raz et al. (1994) *Proc. Natl. Acad. Sci. USA* 91:9519–9523. Such studies have investigated particle-mediated delivery of nucleic acid-based vaccines to both superficial skin and muscle tissue.

Particle-mediated methods for delivering nucleic acid preparations are known in the art. Thus, once prepared and suitably purified, the above-described nucleic acid molecules can be coated onto carrier particles using a variety of techniques known in the art. Carrier particles are selected from materials which have a suitable density in the range of particle sizes typically used for intracellular delivery from a gene gun device. The optimum carrier particle size will, of course, depend on the diameter of the target cells.

For the purposes of the invention, tungsten, gold, platinum and iridium carrier particles can be used. Tungsten and gold particles are preferred. Tungsten particles are readily available in average sizes of 0.5 to 2.0 $\mu$m in diameter. Gold particles or microcrystalline gold (e.g., gold powder A1570, available from Engelhard Corp., East Newark, N.J.) will also find use with the present invention. Gold particles provide uniformity in size (available from Alpha Chemicals in particle sizes of 1–3 $\mu$m, or available from Degussa, South Plainfield, N.J. in a range of particle sizes including 0.95 am). Microcrystalline gold provides a diverse particle size distribution, typically in the range of 0.5–5 $\mu$m. However, the irregular surface area of microcrystalline gold provides for highly efficient coating with nucleic acids.

A number of methods are known and have been described for coating or precipitating DNA or RNA onto gold or tungsten particles. Most such methods generally combine a predetermined amount of gold or tungsten with plasmid DNA, $CaCl_2$ and spermidine. The resulting solution is vortexed continually during the coating procedure to ensure uniformity of the reaction mixture. After precipitation of the nucleic acid, the coated particles can be transferred to suitable membranes and allowed to dry prior to use, coated onto surfaces of a sample module or cassette, or loaded into a delivery cassette for use in particular gene gun instruments.

Various particle acceleration devices suitable for particle-mediated delivery are known in the art, and are all suited for use in the practice of the invention. Current device designs employ an explosive, electric or gaseous discharge to propel the coated carrier particles toward target cells. The coated carrier particles can themselves be releasably attached to a movable carrier sheet, or removably attached to a surface along which a gas stream passes, lifting the particles from the surface accelerating them toward the target. An example of a gaseous discharge device is described in U.S. Pat. No. 5,204,253. An explosive-type device is described in U.S. Pat. No. 4,945,050. One example of a helium discharge-type particle acceleration apparatus is the PowderJect XR® instrument (PowderJect Vaccines, Inc., Madison), Wis., which instrument is described in U.S. Pat. No. 5,120,657. An electric discharge apparatus suitable for use herein is described in U.S. Pat. No. 5,149,655. The disclosure of all of these patents is incorporated herein by reference.

Alternatively, particulate nucleic acid compositions can administered transdermally using a needleless syringe device. For example, a particulate composition comprising the nucleic acid molecules of the present invention can be obtained using general pharmaceutical methods such as simple evaporation (crystallization), vacuum drying, spray drying or lyophilization. If desired, the particles can be further densified using the techniques described in commonly owned International Publication No. WO 97/48485, incorporated herein by reference. These particulate compositions can then be delivered from a needleless syringe system such as those described in commonly owned International Publication Nos. WO 94/24263, WO 96/04947, WO 96/12513, and WO 96/20022, all of which are incorporated herein by reference.

Delivery of particles comprising antigens or allergens from the above-referenced needleless syringe systems is practiced with particles having an approximate size generally ranging from 0.1 to 250 μm, preferably ranging from about 10–70 μm. Particles larger than about 250 μm can also be delivered from the devices, with the upper limitation being the point at which the size of the particles would cause untoward damage to the skin cells. The actual distance which the delivered particles will penetrate a target surface depends upon particle size (e.g., the nominal particle diameter assuming a roughly spherical particle geometry), particle density, the initial velocity at which the particle impacts the surface, and the density and kinematic viscosity of the targeted skin tissue. In this regard, optimal particle densities for use in needleless injection generally range between about 0.1 and 25 g/cm$^3$, preferably between about 0.9 and 1.5 g/cm$^3$, and injection velocities generally range between about 100 and 3,000 m/sec. With appropriate gas pressure, particles having an average diameter of 10–70 μm can be accelerated through the nozzle at velocities approaching the supersonic speeds of a driving gas flow.

The particle compositions or coated particles are administered to the individual in a manner compatible with the dosage formulation, and in an amount that will be effective for the purposes of the invention. The amount of the composition to be delivered (e.g., about 0.1 μg to 1 mg, more preferably 1 to 50 μg of the antigen or allergen, depends on the individual to be tested. The exact amount necessary will vary depending on the age and general condition of the individual to be treated, and an appropriate effective amount can be readily determined by one of skill in the art upon reading the instant specification.

In another embodiment of the invention, a method for eliciting a cellular immune response in a subject is provided. The method entails transfecting cells of the subject with a recombinant hybrid HBcAg-antigen encoding sequence using one of the molecules of the present invention (as described herein above) in a priming step, and then administering a secondary composition to the subject in a boosting step, wherein the secondary composition comprises or encodes the same antigen as in the recombinant hybrid HBcAg-antigen molecule. The secondary composition can be any suitable vaccine composition which contains a nucleic acid molecule encoding the antigen(s) interest, or a composition containing the antigen(s) of interest in peptide or protein form. Direct delivery of the secondary compositions in vivo will generally be accomplished with or without viral vectors (e.g., a modified vaccinia vector) as described above, by injection using either a conventional syringe, or using a particle-mediated delivery system as also described above. Injection will typically be either subcutaneously, epidermally, intradermally, intramucosally (e.g., nasally, rectally and/or vaginally), intraperitoneally, intravenously, orally or intramuscularly. Other modes of administration include oral and pulmonary administration, suppositories, and transdermal applications. Dosage treatment may be a single dose schedule or a multiple dose schedule.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Construction of Hybrid HBcAg-Antigen Molecules

A sequence encoding a HBcAg particle was obtained which had the C-terminal arginine-rich region removed (which deletion does not interfere with particle formation). A unique restriction site (a BSP120I site) was then inserted into the ICE to provide an insertion point for antigens of interest. The resulting sequence is depicted below as SEQUENCE ID NO. I, wherein the BSP120I site is indicated by the boxed sequence region.

```
ATG GAC ATT GAC CCT TAT AAA GAA TTT GGA GCT ACT GTG GAG    (SEQUENCE ID NO.1)
TTA CTC TCG TTT TTG CCT TCT GAC TTC TTT CCT TCC GTC AGA
GAT CTC CTA GAC ACC GCC TCA GCT CTG TAT CGG GAA GCC TTA
GAG TCT CCT GAG CAT TGC TCA CCT CAC CAC ACC GCA CTC AGG
CAA GCC ATT CTC TGC TGG GGG GAA TTG ATG ACT CTA GCT ACC
TGG GTG GGT AAT AAT TTG GAA GAT CCA GCA |GGG CCC| CGG GAT
CTA GTA GTC AAT TAT GTT AAT ACT AAC ATG GGT TTA AAA ATT
AGG CAA CTA TTG TGG TTT CAT ATA TCT TGC CTT ACT TTC GGA
AGA GAG ACT GTA CTT GAA TAT TTG GTA TCT TTC GGA GTG TGG
ATT CGC ACT CCT CCA GCC TAT AGA CCA CCA AAT GCC CCT ATC
TTA TCA ACA CTT CCG GCG CGG CCG CTC TAA.
```

The protein translated from the recombinant nucleic acid molecule of SEQUENCE ID NO 1 is depicted below as SEQUENCE ID NO. 2. Here again, the insertion point (the BSP120I site) for the antigen sequence which contains at least one CTL epitope is indicated by the boxed residues.

```
MDIDPYKEFG ATVELLSFLP SDFFPSVRDL LDTASALYRE ALESPEHCSP    (SEQUENCE ID NO.2)
HHTALRQAIL CWGELMTLAT WVGNNLEDPA |GP|RDLVVNYV NTNMGLKIRQ
LLWFHISCLT FGRETVLEYL VSFGVWIRTP PAYRPPNAPI LSTLPARPL.
```

An antigen sequence encoding an SIV CTL epitope (the mamu A*01-restricted gag sequence: CTPYDINQML (SEQUENCE ID NO: 7) Allen et al. (1998) *J. Immunol.*; Kuroda et al (1988) *J. Exp. Med.* 187:1373–1381), having flanking BSP120I sites, was then inserted into the BSPI20I site of SEQUENCE ID NO. 1 to provide a recombinant molecule encoding a hybrid HBcAg-antigen molecule. The resulting construct is depicted below as SEQUENCE ID NO. 3. The inserted antigen sequence is depicted as the boxed sequence region.

```
ATG GAC ATT GAC CCT TAT AAA GAA TTT GGA GCT ACT GTG GAG  (SEQUENCE ID NO.3)
TTA CTC TCG TTT TTG CCT TCT GAC TTC TTT CCT TCC GTC AGA
GAT CTC CTA GAC ACC GCC TCA GCT CTG TAT CGG GAA GCC TTA
GAG TCT CCT GAG CAT TGC TCA CCT CAC CAC ACC GCA CTC AGG
CAA GCC ATT CTC TGC TGG GGG GAA TTG ATG ACT CTA GCT ACC
TGG GTG GGT AAT AAT TTG GAA GAT CCA GCA GGG CCC GCT GCC
TGC ACA CCC TAT GAC ATT AAC CAG ATG TTA AGA GGG CCC CGG
GAT CTA GTA GTC AAT TAT GTT AAT ACT AAC ATG GGT TTA AAA
ATT AGG CAA CTA TTG TGG TTT CAT ATA TCT TGC CTT ACT TTC
GGA AGA GAG ACT GTA CTT GAA TAT TTG GTA TCT TTC GGA GTG
TGG ATT CGC ACT CCT CCA GCC TAT AGA CCA CCA AAT GCC CCT
ATC TTA TCA ACA CTT CCG GCG CGG CCG CTC TAA.
```

The translation of the recombinant nucleic acid molecule of SEQUENCE ID NO. 3 is depicted below as SEQUENCE ID NO. 4, with the inserted antigen sequence (including the CTL epitope) plus flanking sequences indicated as the boxed residues.

```
MDIDPYKEFG ATVELLSFLP SDFFPSVRDL LDTASALYRE ALESPEHCSP  (SEQUENCE ID NO.4)
HHTALRQAIL CWGELMTLAT WVGNNLEDPA GPAACTPYDI NQMLRGPRDL
VVNYVNTNMG LKIRQLLWFH ISCLTFGRET VLEYLVSFGV WIRTPPAYRP
PNAPILSTLP ARPL.
```

A third sequence comprising the coding sequence for a secretion signal peptide was then linked to the recombinant sequence. This third sequence codes is the coding sequence for the tissue plasminogen activator (tpa) signal peptide, and is depicted below as SEQUENCE ID NO. 5.

```
ATG GAT GCA ATG AAG AGA GGG CTC TGC TGT GTG CTG CTG CTG  (SEQUENCE ID NO.5)
TGT GGA GCA GTC TTC GTT TCG GCT.
```

The protein sequence for this tpa signal peptide is depicted below as SEQUENCE ID NO. 6.

```
MDAMKRGLCC VLLLCGAVFV SA.  (SEQUENCE ID NO.6)
```

The resulting recombinant molecule was then inserted into a plasmid backbone containing the early CMV promoter and Intron A region to obtain an expression cassette. The resulting construct was termed p7262, and the map of this construct is depicted in FIG. 1.

EXAMPLE 2

Immunization with the p7262 Construct

In order to assess the ability of the recombinant molecules of the present invention to elicit high-frequency T-cell responses in immunized subjects, the following study was carried out.

3 rhesus macaque subjects were primed with an expression vector encoding the mamu A*01-restricted gag sequence (CTPYDINQML) (SEQUENCE ID NO: 7) without a carrier moiety. Two of the subjects (monkeys 95045 and 95058) received 6.0 μg DNA total, with 0.5 μg being delivered to each of 12 sites. The third subject (monkey 96031) received 16.0 μg DNA total, with 2.0 μg being delivered to each of 8 sites. The DNA was administered on gold particles using the PowderJect X® gene gun device following known delivery methodology. Subsequently, two of the subjects (monkeys 95045 and 95058) received 4 additional nucleic acid immunization primes using a composition containing the p7262 construct. The first of these additional primes was carried out 13 weeks post initial prime, with each subsequent administration at 46 weeks apart. 16 μg total of the p7262 construct was administered at each additional prime (2 μg to each of 8 sites), again using the PowderJect XR® gene gun device. The third subject (monkey 96031) received 2 additional nucleic acid immunization primes using p7262 composition. The first of these additional primes was carried out 6 weeks post initial prime, with the second administration 4–6 weeks later. 16 μg total of the p7262 construct was administered on each additional prime (2 μg to each of 8 sites) using the PowderJect XR® device.

After the above-described priming immunization regimes, blood samples were taken and peripheral blood mononuclear cells (PBMCs) were isolated and stimulated in vitro for 2 weeks with peptide-pulsed EBV-transformed autologous B cells. The percentage of CD8+ cells specific for the SIV epitope (CTPYDINQML) (SEQUENCE ID NO: 7) was determined for each subject using flow cryometry with a FITC-coupled tetrameric SIV epitope (CTPYDINQML) (SEQUENCE ID NO. 7) using known techniques. Kuroda et al. (1998) *J. Exp. Med.* 187:1373–1381. In addition, SIV epitope (CTPYDINQML) (SEQUENCE ID NO: 7) specific cytolytic activity was determined by measuring lysis against peptide-pulsed autologous B cells in a $^{51}$Cr-release assay. These results are depicted as FIGS. 2A and 2B, respectively. As can be seen, the initial prime resulted in a detectable CTL response. However, the subsequent inoculation with the p7262 construct (containing the recombinant nucleic acid molecule encoding the hybrid HBcAg-antigen) antigen) resulted in a significant increase in the CTL response. In two of these subjects (monkeys 95058 and 96031), the CTL responses were increased to levels exceeding that detected in an SIV-infected monkey (control).

All three of the primed subjects were then boosted with a recombinant modified vaccinia Ankara vector encoding the same SIV epitope (CTPYDINQML) (SEQUENCE ID NO 7).

Hanke et al. (1998) *Vaccine* 16:439–445. More particularly, a secondary vaccine composition containing $5 \times 10^8$ particle forming units (pfu) of a recombinant MVA vector encoding the SIV epitope was administered to each subject. Tetramer staining and killing of peptide-pulsed autologous targets was again assessed in each subject. The results are reported in Table 1 below (tetramer staining and cytolytic activity from fresh or frozen unrestimulated PBMCs). PBMC were assayed one week following the MVA boost.

TABLE 1

| Subject | Tetramer Staining (fresh, unstimulated PBMC) | Cytolytic Activity (frozen, unstimulated PBMC) |
| --- | --- | --- |
| 95058 | 18.0% | 14% |
| 96031 | 8.3% | 7% |
| 95045 | 0.8% | −2% |

As can be seen, extremely high-frequency CTL responses were seen in ⅔ of the subjects (monkeys 95038 and 96031), with 18 and 8.3%, respectively, of the total CD8+ cells specific for the SIV epitope. These levels exceed levels induced by acute SIV infection, exceed levels detected in monkeys primed and boosted with two doses of the MVA vaccine composition (Seth & Letvin (1998) *Proc. Natl. Acad. Sci. USA*), and exceed levels detected in monkeys primed with two DNA immunizations of a non-HBcAg carrier-based SIV epitope. In addition, the inventors believe that the high-frequency CTL response elicited with the recombinant nucleic acid molecules of the present invention may be the highest levels of vaccine-induced CTI ever detected in a nonhuman primate model.

The following general methods were used to carry out the studies described in Examples 3–7 below. In each study, DNA molecules containing HbcAg hybrid sequences were coated onto gold particles in order to provide exemplary compositions according the present invention. The coated particles were administered to animal subjects, and the ability of the compositions to elicit antigen-specific Th, CTL and/or antibody responses was assessed.

Coating the Core Carrier Particles: Appropriate weights of gold particles were weighted directly into 1.5 mL Eppendorf tubes. 400–500 μL of a 0.05M spermidine was then added, and clumps of gold in the gold/spermidine solution were broken-up using a water bath sonicator for 3–5 seconds. DNA stock solution, containing the relevant DNA plasmid molecule, was added to the gold/spermidine solution to result in a bead loading rate of 2.0 μg DNA/mg Au, and the tubes were capped and inverted to mix, then vortexed briefly. After adjusting the vortexer speed down, and while vortexing gently, a volume of 10% $CaCl_2$ was added dropwise to an amount equal to the volume of spermidine added to the dry gold. Once the entire volume of $CaCl_2$ was added, the resultant solution was vortexed at high speed for about 5 seconds. The solution was then allowed to precipitate at room temperature for at least 10 minutes. Meanwhile, a polyvinylpyrrolidone (PVP)/ethanol stock solution was formed at a concentration of 0.03 mg PVP/mL EtOH. After the ten minute precipitation, the tubes were centrifuged briefly (10–15 seconds) to pellet all of the gold. The supernatant was aspirated, and the tubes were "raked" across an Eppendorf rack to loosen the gold pellet. 800 μL of EtOH was added, and the tubes were inverted several times to wash the DNA-coated gold. This step was repeated twice, after which the tubes were again centrifuged and the supernatant aspirated. The washed DNA-coated gold particles were then added to the PVP stock solution, and 50 μg of Quil A was added to the PVP-DNA-coated gold particle solution with sonication for 3 seconds. The resulting particles, which were coated with the DNA+Quil A vaccine composition were then loaded into lengths of Tefzel™ tubing as previously described. See e.g., PCT patent application PCT/US95/00780 and U.S. Pat. Nos. 5,733,600; 5,780,100; 5,865,796 and 5,584,807, the disclosures of which are hereby incorporated by reference.

Mouse ELISPOT Assays: The materials and reagents were as follows. Coating antibodies included Rat anti-mouse IFN-γ Ab, Rat anti-mouse IL-4 AB or Rat anti-mouse IL-5 Ab (Pharmigen); detecting antibodies included Biotinylated rat anti-mouse IFN-γ, Biotinylated rat anti-mouse IL4 or Biotinylated rat anti-mouse IL-5 (Pharmingen); sterile-filtered carbonate buffer pH 9.6 (Pierce), 96 well ELISPOT plates (Millipore), sterile 1× phosphate buffered saline (PBS, Gibco), streptavidin alkaline phosphatase conjugate (Mabtech); Alkaline phosphatase substrate kit (BioRad), and RPMI-10% FCS cell culture medium (Sigma). Cell stimulation was carried out as follows. For T-Helper Cell Cytokine Release, splenocytes from the vaccinated animals were cultured at $6 \times 10^6$ cells/mL in RPMI-10% FCS supplemented with sodium pyruvate and non-essential amino acids. One mL of cells were transferred to each well of a 24 well plate and, for each subject, one well=media only (for background control), and one well=antigen of choice or Class II peptide of choice. The plates were then incubated in a tissue culture incubator for 3 days. For CTL Precursor IFN-γ Release, splenocytes from the vaccinated animals were cultured at $6 \times 10^6$ cells/mL in RPMI-10% FCS supplemented with sodium pyruvate and non-essential amino acids. One mL of cells were transferred to each well of a 24 well plate and the plate was incubated for 2 days, after which CTL peptide was added to peptide wells. For each subject, one well=media only, one well =CTL peptide of choice at $10^{-5}$M, and one well=irrelevant CTL peptide. The plates were then incubated for an additional 24 hours after addition of peptide and prior to plating cells into ELISPOT plate.

Coating and blocking of the ELISPOT plates was carried out as follows. The ELISPOT plates were coated one day prior to plating cells using 50 μL per well of 15 μg/mL coating antibody in sterile carbonate buffer, pH 9.6. The coated plates were incubated overnight at 4° C., after which they were washed six times with 100 μL PBS to remove unbound coating Ab, and then gently blotted. Each well was blocked using 200 μL RPMI-10% FCS for 1–2 hours in a tissue culture incubator at room temperature. All blocking media was removed immediately prior to plating the cells. The cells were plated as follows. After 3 days, cells and supernatant were collected from each well and transferred to a 15 mL conical tube. The cells were spun down in a centrifuge to collect supernatant which was then stored at −80° C. until used in cytokine ELISA analyses. The pelleted cells were resuspended in 2–5 mL media, and then brought to a final concentration of $1 \times 10^7$/mL. The cells were added to the ELISPOT wells at $1 \times 10^6$/well.

The ELISPOT plates were developed as follows. The cells were flicked out and the plates washed two times with PBS using a squirt bottle. The wells were washed with DI water (leaving the water in the wells for a few minutes to lyse the remaining cells), and the plates were washed two more times. Detection antibody was diluted to 1 μg/mL in sterile PBS and then added at 50 μL/well and incubated for 2 hours at room temperature. The plates were washed five times with PBS, and 50 μL strepavidin alkaline phosphatase conjugate (diluted 1:1000 in PBS) and the plates were incubated at room temperature for 2 hours. The plates were then washed five times with PBS, and 50 μL of chromogenic alkaline phosphatase substrate was added and the plates allowed to incubate at room temperature until dark spots emerge (about 2 hours). The color reaction was stopped by washing three times with 200 μL of tap water, the plates allowed to air dry, and the spots counted under a dissecting microscope (40×).

Mouse Peptide-Pulsed CTL Assays: The materials and reagents were as follows. RPMI-10 Media (500 mL RPMI 1640 with L-glutamine and Hepes, 55 mL heat-inactivated fetal bovine serum (FBS), 0.5 mL gentamycin, 5.5 mL antibiotics antimycolic solution); Sensitization Media ("SM") without IL-2 (500 mL RPMI-10, 5.0 mL 100 mM Na Pyruvate, 5.0 mL 100X nonessential amino acids); and SM with IL-2 (SM with final concentration of 20 U/mL recombinant rat IL-2); CTL epitope peptide (peptide dissolved in tissue culture grade DMSO to stock concentration of $10^{-2}$M); ACK lysis buffer (Biowhittaker); recombinant rat IL-2 (Collaborative); Mitomycin C C (Aldrich dissolved in sterile PBS to obtain 500 µg/mL stock solution; 50 mL conical tubes (Falcon), nylon mesh strainer cup inserts (Falcon); $^{51}$Chromium and Lumaplates (Packard).

For peptide-pulsed stimulators, naive syngeneic spleens are provided (approx. 1.2×1 stimulators/mouse) by collecting spleens and grinding by pressing between two autoclaved frosted slides to break up the sac and release the cells into a small petri dish. Cell clumps are broken up by pipetting the cells up and down with a 3 mL transfer pipet, and the resulting cell suspension is passed through a 70 µm nylon cell strainer into a 50 mL conical tube using 5–10 mL RPMI-10 media to wash the cells through. The recovered splenocytes are spun at 1500 rpm for 5 minutes to pellet, and the supernatant discarded. The RBCs were lysed by resuspending the splenocytes in 5 mL ACK lysis buffer for 1–2 minutes, after which the cells were washed twice with 20 mL unsupplemented RPMI and once with RPMI-10. The cells were then resuspended at approximately $1\times10^7$ cells/mL. For the HbsAg CTL assay, a P815 cell line was transformed with the HbsAg sequence and used as the stimulator cells. The stimulators were treated with mitomycin C (for each 10 mL cells, 500 µL of 0.5 mg/mL mitomycin C was added), and the cells were incubated with the mitomycin C for 2545 minutes at 37° C., 5% $CO_2$. After treatment, the cells were washed twice with unsupplemented RPMI and once with RPMI-10. The washed cells were resuspended to $2\times10^6$ cells/mL in SM with 20 U/mL rat IL-2, and the stock CTL epitope peptide added. The stimulator cells were dispensed at a ratio of 3/1 responder/stimulator into 24-well plates and incubated overnight at 37° C., 5% $CO_2$.

The in vitro stimulation of responder cells was carried out as follows. Spleens were collected from vaccinated and control mice, and responder splenocytes were isolated by grinding the spleens as described above. RBCs were lysed with 5 mL ACK lysis buffer for 2–3 minutes, and the cells were washed two times with 20 mL unsupplemented RPMI and once with RPMI-10. The splenocytes were then resuspended at $6\times10^6$ cells/mL in SM without IL-2. For each mouse, 1 mL of splenocytes were dispensed into each well of a 24-well plate containing 1 mL of the $2\times10^6$ cells/mL peptide-pulsed stimulator cells described above in SM with IL-2 (final concentration of IL-2 was 10U/mL), and the plates incubated at 37° C., 5% $CO_2$ for 5–7 days.

CTL $^{51}$Chromium Release Assay: For peptide-specific lysis, the following techniques were used. Log-phase syngeneic target cells were plated in 96 well plates at approximately 30,000 targets/well. An appropriate amount of target cells were pelleted in conical tubes and resuspended in 20 µL heat-inactivated FBS. 100–200 µL of $^{51}$Cr (sodium chromate) was added to each pellet, mixed well, then incubated for 1 hour at 37° C. The cells were then washed four times with 6–10 mL RPMI-10 per pellet, and then resuspended at $3\times10^5$ cells/mL in RPMI-10. For peptide-pulsed targets, an appropriate amount of the stock Ctl epitope peptide was added to reach a final optimal peptide concentration (approximately $10^{-M}$). Target cells were allowed to pulse with the peptides for at least 30 minutes (at 37° C.) prior to plating with the effector cells. Alternatively, the p815/HBsAg cell line was used as the target.

After 5–7 days of in vitro stimulation, effector splenocytes were collected from the 24-well plates and the cells from each mouse were pooled in 15 mL conical tubes, and then resuspended at 1.5×1 7 cells/mL. For plating, splenocytes from each mouse were plated at 50, 17, 5.6 and 1.9 effector/target ratios. After dilutions, 100 µL of the $^{51}$Cr-labeled targets were added to each well. The plates were spun briefly and then incubated 4–6 hours at 37° C. Lysis was measured against both peptide-pulsed and unpulsed control targets for each mouse.

For nonspecific lysis, the same protocol was followed except that 100 µL of unpulsed targets were also plated. After a 4–6 hour incubation, the plates were spun to pellet the cells and lysed. 40 µL of the supernatant was then transferred to 96-well plates each well containing 200 µL of scintillation fluid, and the plates were allowed to dry for 2 hours or overnight. The plates were sealed and counted using a standard program for $^{51}$Cr liquid. To calculate % Lysis, (test cpm-spont. cpm) was divided by (max. cpm-spont. cpm) and multiplied by 100. To obtain % specific lysis, the % lysis of unpulsed targets was subtracted from the % lysis of peptide-pulsed targets.

ELISA: Antibody response to the various vaccine compositions was determined by a standard ELISA procedure. More particularly, high-affinity binding plates (Costar) were coated with 50 µL/well with a 8 µg/mL antigen stock solution (in PBS) and incubated overnight at 4° C. The antigen solution was aspirated and the plates blocked with 2% BSA/PBS for at least one hour at room temperature. The plates were washed three times with wash buffer (PBS/0.025% Tween-20), and 50 µL of sample serum added and incubated for two hours at room temperature (dilution buffer: 2% BSA/PBS). The plates were washed three times and incubated with conjugated labelled goat antibodies specific for mouse immunoglobulin IgG or specific IgG subclasses for 1 hr at room temperature. Following three additional washes, the ELISA plates were incubated with label conjugates for 1 hr at room temperature. Finally, plates were washed and developed with a suitable substrate (HRP, alkaline phosphatase, etc. kits from Bio-Rad, Richmond, Calif.) and allowed to develop for 30 minutes. Reactions were stopped with 1N $H_2SO_4$ or 0.4M NaOH, and the plates read at $A_{450}$ or $A_{405}$ depending on the label used. Mean background absorbance was determined by wells that received all reagents except for test sera. Endpoint titers were determined as the highest dilution resulting in an absorbance reading of 50% over background absorbance.

EXAMPLE 3

Induction of Hepatitis B Surface Antigen (HbsAg)-Specific CTL Using a Hybrid HBcAg/T Cell Epitope DNA Vaccine Expression vector pWRG7086 was constructed by inserting a mouse H2-d class I restricted minimal CTL epitope for hepatitis B surface antigen (IPQSLDSWWTSL (SEQUENCE ID NO. 8), Luca et. al. *Proc. Natl. Acad. Sci. USA* 91:3764–68) into the ICE loop region of HBcAg. The HBcAg/CTL epitope fusion was inserted into an expression cassette containing the early CMV promoter and Intron A region. The vector was coated onto gold particles as described above.

5 Mice received 2 DNA immunizations (via a PowderJect XR gene gun device) each immunization consisting of 0.5 µg of either pWRG7086 or pWRG7031 (positive control) or control DNA spaced 4 weeks apart.

Splenocytes were harvested 6 months following the second immunization using a P815 cell line to restimulate in vitro and assayed for cytolytic activity using the standard Cr51-release assay described above. The results are reported in Table 2 below. As can be seen, epitope-specific T cell responses were induced in the immunization strategy.

TABLE 2

| Group | No. Mice | Ave % specific lysis (50:1) |
|---|---|---|
| WRG7086 | 2 | 33 |
| WRG7031 (Full length HBsAg, positive, control) | 2 | 61 |
| Negative control | 1 | 7 |

EXAMPLE 4

Induction of HIV-Specific Antibody Response Using a Hybrid HBcAg/Antigen DNA Vaccine Expression vector pWRG7094 was constructed by inserting immunodominant sequences of the V3 hypervariable loop (RRITSGPGKVLYTTGEII) (SEQUENCE ID NO. 9) from the envelope gene of $HIV_{SF33}$ into the ICE region of HBcAg. The HBcAg/$HIV_{SF33}$ B cell epitope fusion was inserted into an expression cassette containing the early CMV promoter and Intron A region. The vector was coated onto gold particles as described above.

4 Mice received 3 DNA immunizations (via a PowderJect XR gene gun device), each immunization consisting of 0.5 μg pWRG7094, spaced 2–4 weeks apart. The mice were bled 2 weeks following each immunization. Serum anti-$HIVgp120_{SF33}$ responses were evaluated using recombinant $HIVgp120_{SF33}$ (Chiron Corp., Emeryville, Calif.) as capture antigen in a standard ELISA (see appendix II). The serum anti-$HIVgp120_{SF33}$ responses (reciprocal endpoint titer) following immunization with pWRG7094 are reported below in Table 3. As can be seen, an antigen-specific antibody response was induced using the hybrid HBcAg/epitope molecules of the present invention.

TABLE 3

| Mouse # | Post-prime | Post-boost 1 | Post-boost 2 |
|---|---|---|---|
| 1 | 300 | 20,000 | 70,000 |
| 2 | 0 | 5,000 | 250,000 |
| 3 | 300 | 20,000 | 32,000 |
| 4 | 1000 | 70,000 | 128,000 |

EXAMPLE 5

Induction of Malaria-Specific Antibody Response Using a Hybrid HBcAg/Antigen DNA Vaccine Expression vector pWRG7108 was constructed by inserting 2 tandem copies of the immunodominant B cell epitope from the circumsporozoite (CS) gene of *Plasmodium berghei* (DPPPPNPNDPPPPNPN) (SEQUENCE ID NO. 10) into the ICE region of HBcAg. The HBcAg/berghei epitope fusion was inserted into an expression cassette containing the early CMV promoter and Intron A region. The vector was coated onto gold particles as described above.

4 Mice received 3 DNA immunizations (via a PowderJect XR gene gun device), each immunization consisting of 0.5 μg pWRG7110, spaced 2–4 weeks apart. The mice were bled 2 weeks following each immunization. Serum anti-*P. berghei* responses were evaluated using purified *P. berghei* sporozoites (1000/well) as capture antigen in the standard ELISA described above).

Antibody responses in these mice were compared to antibody responses induced in mice immunized with DNA expressing the full-length *P. berghei* CS gene (pWRG6518).

The results are reported below in Table 4. As can be seen, the hybrid HBcAg/Antigen constructs of the present invention induce higher titer antibody responses that immunization with DNA encoding the epitope in its natural context within the full-length *P. berghei* gene.

TABLE 4

Anti-PbCS Reciprocal endpoint titers

| Mouse | DNA | Post-prime | Post-boost 1 | Post-boost 2 |
|---|---|---|---|---|
| n = 7 | CMV-Pb-CS (pWRG6518) | <10 | <10 | 10–400 |
| 13 | HBcAg-CS epitope (pWRG7108) | 3,600 | 13,000 | 40,000 |
| 14 | HBcAg-CS epitope (pWRG7108) | 900 | 80,000 | 160,000 |
| 15 | HBcAg-CS epitope (pWRG7108) | 1,800 | 80,000 | 160,000 |
| 16 | HBcAg-CS epitope (pWRG7108) | 1,800 | 26,000 | 40,000 |

EXAMPLE 6

Induction of FMDV-Specific Neutralizing Antibody Response Using a Hybrid HBcAg/Antigen DNA Vaccine Two expression vectors were constructed. Expression vector pWRG7159 was constructed by inserting a single copy of the neutralization epitope (GSGVRGDFGSLAPRVARQLP) (SEQUENCE ID NO. 11) from the envelope gene of Foot and Mouth Disease Virus (FMDV) into each of the ICE and carboxy regions of HBcAg. Expression vector pWRG7165 contains a single copy of the neutralization epitope inserted in the ICE region of HBcAg. The vectors were coated onto separate lots of gold particles as described above.

8 Mice received 3 DNA immunizations (via a PowderJect XR gene gun device), each immunization consisting of 0.5 μg or either the pWRG7159 or pWRG7165 DNA, wherein the immunizations were spaced 2–4 weeks apart. The mice were bled 2 weeks after each immunization and serum assayed for FMDV-specific antibody by ELISA using peptide representing the IDR as capture antigen. Serum antibodies were also tested for the ability to neutralize FMDV in a virus neutralization assay (F. Brown, Plum Island Institute).

The results are reported in Table 5 below. As can be seen, the hybrid DNA constructs of the present invention can induce a neutralizing antibody response against the antigen of interest.

TABLE 5

| Mouse | DNA | ELISA titer post-prime | ELISA titer post-boost 1 | ELISA titer Post-boost 2 | Log virus Neutralization titer by serum diluted 1/100* (Post-boost 2) |
|---|---|---|---|---|---|
| 5 | 7159 | 8800 | 52000 | 41000 | 1.5 |
| 6 | 7159 | 12000 | 59000 | 94000 | 3.0–3.5 |
| 7 | 7159 | 5000 | 44000 | 49000 | 0 |

TABLE 5-continued

| Mouse | DNA | ELISA titer post-prime | ELISA titer post-boost 1 | ELISA titer Post-boost 2 | Log virus Neutralization titer by serum diluted 1/100* (Post-boost 2) |
|---|---|---|---|---|---|
| 8 | 7159 | 5000 | 62000 | 83000 | 3.5 |
| 8 | 7165 | 24000 | 83000 | 90000 | 3.0 |
| 10 | 7165 | 13000 | 42000 | 44000 | 3.0 |
| 11 | 7165 | 14000 | 15000 | 12000 | 1.5 |
| 12 | 7165 | 15000 | 36000 | 37000 | 0.5–1.0 |

*A log virus neutralization titer of 3.0 to 3.5 is considered a very good titer.

EXAMPLE 7

Immunization Study Using a Hybrid HBcAg/ Antigen DNA Vaccine

In order to demonstrate the superiority of DNA immunization using the hybrid HBcAg molecules of the present invention, the following study is carried out. This study will establish that administration of DNA encoding HBcAg/epitope fusion will provide an advantage over existing methodologies. Specifically, HBcAg/epitope DNA immunization will: (1) enhance immunogenicity of DNA-based immunization of epitopes; and (2) provide expression of the fusion product in the host cells in its natural conformation and in addition, through intracellular expression provide access to both the class I and class II pathways for superior induction of both CD8+ and CD4+ immune responses.

The following vaccines containing the mouse H2-d-class I restricted minimal CTL Epitope (RGPGRAFVTI (SEQUENCE ID NO. 12) Takeshita T., et. al. (1995) *J. Immunol.* 154: 1973–86) of $HIV_{LAI}$ gp120 are constructed and compared for induction of epitope-specific CTL responses in mice.

(a)—HIV gp120 CTL epitope encoded in the conventional plasmid: CMV-intronA-RGPGRAFVTI (R>I)-pal.

(b)—HIV gp120 CTL epitope encoded as a fusion to HBcAg: CMV-intron A-HBcAg/R>I-pal.

(c)—HIV gp120 CTL epitope encoded as a fusion to HBcAg, expressed in mammalian cells, and purified as recombinant protein (rHBcAg/R>I)

(d)—Entire HIV gp 120 gene expressed in the conventional plasmid CMV-intron A-HIV gp120-pal.

Vaccine Preparation:

The expression vectors for groups (a) and (b) are constructed as per previously established methods. The expression vector from (a) is expressed in a Balb/C cell line or yeast and purified as previously described. The expression vector for group (d) has been constructed (Fuller et al. (1994) AIDS Res. and Hum. Retroviruses).

Immunizations:

Mice are immunized at least two times with 0.5 µg DNA on 0.5 mg gold beads with the PowderJect XR gene gun device or injected with two doses of 1–5 µg HBcAg/R>I protein in PBS per dose, spaced 4 weeks apart.

Assays:

Splenocytes and blood are collected from two sets of mice two weeks following the first or second immunization. The frequency of CD8+ T cell responses is compared by ELISPOT analysis (see above) and by $^{51}$Cr-release assay (see above).

Antibody responses to HBcAg and HIVgp120 is measured to confirm successful immunization.

Accordingly, novel recombinant nucleic acid molecules, compositions comprising those molecules, and nucleic acid immunization techniques have been described. Although preferred embodiments of the subject invention have been described in some detail, it is understood that obvious variations can be made without departing from the spirit and the scope of the invention as defined by the appended claims.

We claim:

1. A recombinant nucleic acid molecule comprising a first nucleic acid sequence encoding a Hepatitis B virus core antigen, wherein said first nucleic acid sequence comprises a primary immunodominant core epitope (ICE) region, and a second nucleic acid sequence encoding an antigen comprising at least one cytolytic T lymphocyte (CTL) epitope, wherein said second nucleic acid sequence is heterologous to said first nucleic acid sequence and is inserted into the ICE region of the first nucleic acid sequence, and wherein the recombinant nucleic acid molecule elicits a CTL response to said CTL epitope in a subject.

2. The nucleic acid molecule of claim 1 further comprising a third nucleic acid sequence which encodes a peptide leader sequence that provides for secretion of an attached peptide sequence from a mammalian cell, wherein the first, second and third nucleic acid sequences are linked together to form a hybrid sequence, and said third nucleic acid sequence is arranged in the molecule in a 5' upstream position relative to the first and second sequences.

3. An expression cassette comprising a promoter sequence operably linked to and controlling the expression of the nucleic acid molecule of claim 1.

4. A vector comprising the expression cassette of claim 3.

5. A composition of matter comprising a gold particle coated with copies of the vector of claim 4.

6. A composition of matter comprising the vector of claim 4 combined with a pharmaceutically acceptable carrier or excipient.

7. The nucleic acid molecule of claim 1 wherein the second nucleic acid sequence consists essentially of nucleotides that encode the CTL epitope.

8. The nucleic acid molecule of claim 1 wherein the first nucleic acid sequence encodes a Hepatitis B virus core antigen from which the C-terminal arginine-rich region has been removed.

9. The nucleic acid molecule of claim 1 wherein the antigen is an antigen of a viral, bacterial, parasite or fungal pathogen.

10. A recombinant nucleic acid molecule comprising a first nucleic acid sequence encoding a Hepatitis B virus core antigen from which the primary immunodominant core epitope (ICE) region has been removed, and a second nucleic acid sequence encoding an antigen comprising at least one cytolytic T lymphocyte (CTL) epitope, wherein the second nucleic acid sequence is heterologous to the first nucleic acid sequence, and wherein the first and second nucleic acid sequences are linked together to form a hybrid sequence, and wherein the recombinant nucleic acid molecule elicits a CTL response to said CTL epitope in a subject.

11. The nucleic acid molecule of claim 10 further comprising a third nucleic acid sequence which encodes a peptide leader sequence that provides for secretion of an attached peptide sequence from a mammalian cell, wherein the first, second and third nucleic acid sequences are linked together to form a hybrid sequence, and said third nucleic acid sequence is arranged in the molecule in a 5' upstream position relative to the first and second sequences.

12. An expression cassette comprising a promoter sequence operably linked to and controlling the expression of the nucleic acid molecule of claim 10.

13. A vector comprising the expression cassette of claim 12.

14. A composition of matter comprising a gold particle coated with copies of the vector of claim 13.

15. A composition of matter comprising the vector of claim 13 combined with a pharmaceutically acceptable carrier or excipient.

16. The nucleic acid molecule of claim 10 wherein the second nucleic acid sequence consists essentially of nucleotides that encode the CTL epitope.

17. The nucleic acid molecule of claim 10 wherein the first nucleic acid sequence encodes a Hepatitis B virus core antigen from which the C-terminal arginine-rich region has been removed.

18. The nucleic acid molecule of claim 10 wherein the antigen is an antigen of a viral, bacterial, parasite or fungal pathogen.

19. A method of eliciting a cytolytic T lymphocyte (CTL) response in a subject, said method comprising:

(a) transfecting cells of the subject with a recombinant nucleic acid molecule encoding a hybrid molecule comprising a Hepatitis B core antigen carrier component and a target antigen component, wherein the target antigen component comprises at least one CTL epitope of interest and the target antigen component is heterologous to the Hepatitis B core antigen carrier component, wherein said transfecting is carried out under conditions that permit expression of said hybrid molecule within said subject, wherein said transfecting is conducted ex vivo or in vivo by subcutaneous or intradermal administration; and (b) administering a secondary composition to the subject, wherein said secondary composition comprises said at least one CTL epitope from the target antigen, and the combination of steps (a) and (b) is sufficient to elicit a CTL response against the target antigen.

20. The method of claim 19 wherein the hybrid molecule comprises the at least one cytolytic T lymphocyte (CTL) epitope of interest inserted within the primary immunodominant core epitope (ICE) region in the Hepatitis B core antigen carrier component.

21. The method of claim 19 wherein the recombinant nucleic acid molecule encodes a hybrid molecule having a Hepatitis B core antigen carrier component, a target antigen component comprising at least one cytolytic T lymphocyte (CTL) epitope of interest, and a peptide leader sequence that provides for secretion of an attached peptide sequence from a mammalian cell.

22. The method of claim 19, wherein the secondary composition comprises a recombinant viral vector which includes a nucleic acid sequence encoding said at least one CTL epitope from the target antigen.

23. The method of claim 22 wherein the recombinant viral vector is a vaccinia virus vector.

24. The method of claim 19 wherein the transfecting step is carried out in vivo using a particle-mediated transfection technique.

25. The method of claim 19 wherein the transfecting step is carried out ex vivo to obtain transfected cells which are subsequently introduced into said subject prior to step (b).

26. The method of claim 19 wherein the subject is human.

27. The nucleic acid molecule of claim 1, wherein at least one cytolytic T lymphocyte (CTL) epitope comprises eight or more amino acids.

28. The nucleic acid molecule of claim 1, wherein at least one cytolytic T lymphocyte (CTL) epitope comprises nine to ten amino acids.

29. A method of eliciting a cytolytic T lymphocyte (CTL) response in a subject comprising administering subcutaneously or intradermally to the subject the recombinant nucleic acid molecule of claim 1.

30. A method of eliciting a cytolytic lymphocyte (CTL) response in a subject comprising administering subcutaneously or intradermally to the subject the recombinant nucleic acid molecule of claim 10.

* * * * *

SEQUENCE LISTING

<160> NUMBER OF SEQ ID NOS: 12

<210> SEQ ID NO 1
<211> LENGTH: 450
<212> TYPE: DNA
<213> ORGANISM: Artificial Sequence
<220> FEATURE:
<223> OTHER INFORMATION: Description of Artificial Sequence:synthetic construct

<400> SEQUENCE: 1

```
atggacattg acccttataa agaatttgga gctactgtgg agttactctc gttttttgcct      60 tctgacttct ttccttccgt cagagatctc ctagacaccg cctcagctct gtatcgggaa     120
gccttagagt ctcctgagca ttgctcacct caccacaccg cactcaggca agccattctc     180 tgctggggg aattgatgac tctagctacc tgggtgggta ataatttgga agatccagca     240
gggccccggg atctagtagt caattatgtt aatactaaca tgggtttaaa aattaggcaa     300
ctattgtggt ttcatatatc ttgccttact ttcggaagag agactgtact tgaatatttg     360
gtatctttcg gagtgtggat tcgcactcct ccagcctata gaccaccaaa tgcccctatc     420
ttatcaacac ttccggcgcg gccgctctaa                                       450
```

<210> SEQ ID NO 2
<211> LENGTH: 149
<212> TYPE: PRT
<213> ORGANISM: Artificial Sequence
<220> FEATURE:
<223> OTHER INFORMATION: Description of Artificial Sequence:synthetic construct

<400> SEQUENCE: 2

```
Met Asp Ile Asp Pro Tyr Lys Glu Phe Gly Ala Thr Val Glu Leu Leu
 1               5                  10                  15

Ser Phe Leu Pro Ser Asp Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Gly Pro Arg Asp Leu Val Val Asn Tyr Val Asn Thr Asn Met Gly Leu
                85                  90                  95

Lys Ile Arg Gln Leu Leu Trp Phe His Ile Ser Cys Leu Thr Phe Gly
            100                 105                 110

Arg Glu Thr Val Leu Glu Tyr Leu Val Ser Phe Gly Val Trp Ile Arg
        115                 120                 125

Thr Pro Pro Ala Tyr Arg Pro Pro Asn Ala Pro Ile Leu Ser Thr Leu
    130                 135                 140

Pro Ala Arg Pro Leu
145
```

<210> SEQ ID NO 3
<211> LENGTH: 495
<212> TYPE: DNA
<213> ORGANISM: Artificial Sequence
<220> FEATURE:
<223> OTHER INFORMATION: Description of Artificial Sequence:synthetic construct

<400> SEQUENCE: 3

```
atggacattg accecttataa agaatttgga gctactgtgg agttactctc gttttttgcct      60 tctgacttct ttccttccgt cagagatctc ctagacaccg cctcagctct gtatcgggaa     120
gccttagagt ctcctgagca ttgctcacct caccacaccg cactcaggca agccattctc     180
tgctgggggg aattgatgac tctagctacc tgggtgggta ataatttgga agatccagca     240
gggcccgctg cctgcacacc ctatgacatt aaccagatgt taagagggcc ccggatcta      300 gtagtcaatt atgttaatac taacatgggt ttaaaaatta ggcaactatt gtggtttcat     360
atatcttgcc ttactttcgg aagagagact gtacttgaat atttggtatc tttcggagtg     420
tggattcgca ctcctccagc ctatagacca ccaaatgccc tatcttatc aacacttccg      480 gcgcggccgc tctaa                                                      495
```

<210> SEQ ID NO 4
<211> LENGTH: 164
<212> TYPE: PRT
<213> ORGANISM: Artificial Sequence
<220> FEATURE:
<223> OTHER INFORMATION: Description of Artificial Sequence:synthetic construct

<400> SEQUENCE: 4

```
Met Asp Ile Asp Pro Tyr Lys Glu Phe Gly Ala Thr Val Glu Leu Leu
 1               5                  10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Gly Pro Ala Ala Cys Thr Pro Tyr Asp Ile Asn Gln Met Leu Arg Gly
                85                  90                  95

Pro Arg Asp Leu Val Val Asn Tyr Val Asn Thr Asn Met Gly Leu Lys
            100                 105                 110

Ile Arg Gln Leu Leu Trp Phe His Ile Ser Cys Leu Thr Phe Gly Arg
        115                 120                 125

Glu Thr Val Leu Glu Tyr Leu Val Ser Phe Gly Val Trp Ile Arg Thr
    130                 135                 140

Pro Pro Ala Tyr Arg Pro Pro Asn Ala Pro Ile Leu Ser Thr Leu Pro
145                 150                 155                 160

Ala Arg Pro Leu

<210> SEQ ID NO 5
<211> LENGTH: 66
<212> TYPE: DNA
<213> ORGANISM: Artificial Sequence
<220> FEATURE:
<223> OTHER INFORMATION: Description of Artificial Sequence:synthetic
      construct

<400> SEQUENCE: 5
atggatgcaa tgaagagagg gctctgctgt gtgctgctgc tgtgtggagc agtcttcgtt      60
tcggct                                                                66

<210> SEQ ID NO 6
<211> LENGTH: 22
<212> TYPE: PRT
<213> ORGANISM: Artificial Sequence
<220> FEATURE:
<223> OTHER INFORMATION: Description of Artificial Sequence:synthetic
      construct

<400> SEQUENCE: 6

Met Asp Ala Met Lys Arg Gly Leu Cys Cys Val Leu Leu Leu Cys Gly
 1               5                  10                  15

Ala Val Phe Val Ser Ala
            20

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence:synthetic
      construct

<400> SEQUENCE: 7

Cys Thr Pro Tyr Asp Ile Asn Gln Met Leu
 1               5                  10
```

-continued

```
<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence:synthetic
      construct

<400> SEQUENCE: 8

Ile Pro Gln Ser Leu Asp Ser Trp Trp Thr Ser Leu
1               5                   10

<210> SEQ ID NO 9
<211> LENGTH: 18
<212> TYPE: PRT
<213> ORGANISM: Artificial Sequence
<220> FEATURE:
<223> OTHER INFORMATION: Description of Artificial Sequence:synthetic
      construct

<400> SEQUENCE: 9

Arg Arg Ile Thr Ser Gly Pro Gly Lys Val Leu Tyr Thr Thr Gly Glu
1               5                   10                  15

Ile Ile

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence:synthetic
      construct

<400> SEQUENCE: 10

Asp Pro Pro Pro Pro Asn Pro Asn Asp Pro Pro Pro Asn Pro Asn
1               5                   10                  15

<210> SEQ ID NO 11
<211> LENGTH: 20
<212> TYPE: PRT
<213> ORGANISM: Artificial Sequence
<220> FEATURE:
<223> OTHER INFORMATION: Description of Artificial Sequence:synthetic
      construct

<400> SEQUENCE: 11

Gly Ser Gly Val Arg Gly Asp Phe Gly Ser Leu Ala Pro Arg Val Ala
1               5                   10                  15

Arg Gln Leu Pro
            20

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence:synthetic
      construct

<400> SEQUENCE: 12

Arg Gly Pro Gly Arg Ala Phe Val Thr Ile
1               5                   10
```